United States Patent
Sondermann et al.

(10) Patent No.: US 10,866,247 B2
(45) Date of Patent: Dec. 15, 2020

(54) IN VITRO METHOD FOR DETERMINING THE STABILITY OF COMPOSITIONS COMPRISING SOLUBLE FC GAMMA RECEPTOR(S)

(71) Applicant: Suppremol GmbH, Martinsried (DE)

(72) Inventors: Peter Sondermann, Stockdorf (DE); Thomas Pohl, Neuried (DE); Dominik Ter Meer, Munich (DE)

(73) Assignee: SUPPREMOL GMBH, Munich (DE)

( * ) Notice: Subject to any disclaimer, the term of this patent is extended or adjusted under 35 U.S.C. 154(b) by 0 days.

(21) Appl. No.: 14/909,009

(22) PCT Filed: Aug. 1, 2014

(86) PCT No.: PCT/EP2014/066646
§ 371 (c)(1),
(2) Date: Jan. 29, 2016

(87) PCT Pub. No.: WO2015/015001
PCT Pub. Date: Feb. 5, 2015

(65) Prior Publication Data
US 2016/0195541 A1   Jul. 7, 2016

(30) Foreign Application Priority Data
Aug. 1, 2013   (EP) .................................... 13003835

(51) Int. Cl.
*G01N 33/53* (2006.01)
*G01N 33/68* (2006.01)
*G01N 33/50* (2006.01)
*C07K 16/00* (2006.01)

(52) U.S. Cl.
CPC ......... *G01N 33/6854* (2013.01); *C07K 16/00* (2013.01); *G01N 33/5047* (2013.01)

(58) Field of Classification Search
CPC ........... G01N 33/6854; G01N 33/5047; G01N 33/55; C07K 16/00
See application file for complete search history.

(56) References Cited

U.S. PATENT DOCUMENTS
2008/0008700 A1   1/2008   Hograth et al.

FOREIGN PATENT DOCUMENTS
EP   1870422 A1   12/2007
WO   2003/043648 A2   5/2003
WO   WO2005023867   *   3/2005   ............ C07K 16/06
WO   2011/039012 A1   4/2011
WO   2012/059308 A1   5/2012
WO   2015/015001 A1   2/2015

OTHER PUBLICATIONS

Sondermann (Biochemistry 1999, 38, 8469-8477).*
Engelhardt et al (Eur. J. Immunol. 1990. 20: 1367-1377).*
Sondermann II (Biol. Chem., vol. 380, pp. 717-721, Jun. 1999).*
Ratcliffe (Immunology Letters vol. 7 issue 2; p. 73-6, Abstract).*
Richter et al (SA Fam Pract 2006;48(8):36-43.*
Lyden et al (J Immunol 2001; 166:3882-3889).*
Luo et al., Dimers and multimers of monoclonal IgGI exhibit higher in vitro binding affinities to Fcgamma receptors. mAbs, vol. 1, No. 5. , pp. 491-504 (2009).
International Search Report and Written Opinion for PCT/EP2014/066646 filed on Aug. 1, 2014.
Martensson et al., Development of an antigen-independent affinity assay to study the binding of IgG to Fc Gamma Receptors. Master's degree project in Protein Science, Mar. 2012. Retrieved from Internet, http://lup.lub.lu.se/record/2863024/file/2863028 (2013).
Bruhns et al., Specificity and affinity of human Fc receptors and their polymorphic variants for human IgG subclasses. Blood, vol. 113, No. 16, pp. 3716-3725 (2009).

* cited by examiner

*Primary Examiner* — Carmencita M Belei
(74) *Attorney, Agent, or Firm* — K&L Gates LLP; Louis C. Cullman; Hal Gibson

(57) ABSTRACT

The present invention relates in essence to an in vitro method for determining the stability, such as the shelf stability; stability over time; shelf life of a composition which comprises or essentially consists of soluble human Fc gamma receptor IIA, MB, IIIA and/or 1 MB, said method comprising the steps of contacting a surface comprising human Fc gamma receptor IIA, MB, IIIA and/or 1 MB with a set amount of aggregated human IgG; contacting said surface comprising human Fc gamma receptor IIA, MB, IIIA and/or 1 MB with a set amount of said composition of soluble human Fc gamma receptor IIA, MB, IIIA and/or 1 MB; determining the amount of aggregated human IgG which is bound to said surface comprising said human Fc gamma receptor IIA, MB, IIIA and/or 1 MB, and comparing the amount of aggregated human IgG which is bound to said surface as determined in step (c) with a reference value and (thereby) determining the stability [shelf stability; stability over time; shelf life] of said composition which comprises or essentially consists of soluble human Fc gamma receptor IIA, MB, IIIA and/or 1 MB. The present invention also relates to aggregated human IgG obtainable by a method as defined herein, as well as to the use of the mentioned aggregated human IgG in the methods of the invention.

9 Claims, 19 Drawing Sheets
Specification includes a Sequence Listing.

Langmuir diagram of data fitted to normalized measured Median values of reference and SM101

| SM101 | Ref. Std. | IMP |
|---|---|---|
| app.$K_D$ [M] | $0.74 \times 10^{-6}$ | $0.90 \times 10^{-6}$ |
| app.$K_A$ [M$^{-1}$] | $1.35 \times 10^{6}$ | $1.11 \times 10^{6}$ |
| $R_{max}$ | 105.64 | 107.21 |
| Residuals | 0.05 | 0.02 |
| $IC_{50}$ [µg/mL] | 12.9 | 16.2 |

| SM101 | | | Median | |
|---|---|---|---|---|
| [μg/μL] | Conc [M] | nM | Signal | norm. Signal |
| 0 | 0.00E+00 | 0.00E+00 | 3877 | 0.00% |
| 0.0078 | 3.90E-07 | 3.90E+02 | 3008 | 23.24% |
| 0.0156 | 7.80E-07 | 7.80E+02 | 2270 | 42.97% |
| 0.03125 | 1.56E-06 | 1.56E+03 | 1242 | 70.45% |
| 0.0625 | 3.13E-06 | 3.13E+03 | 466 | 91.20% |
| 0.125 | 6.25E-06 | 6.25E+03 | 329 | 94.87% |
| 0.25 | 1.25E-05 | 1.25E+04 | 197 | 98.40% |
| 0.5 | 2.50E-05 | 2.50E+04 | 238 | 97.30% |
| | | sec. Ab | 137 | 100.00% |

FIG. 13

| SM101 IMP / Ref. Std. | | | SM101 Ref. Std. | | SM101 IMP | |
|---|---|---|---|---|---|---|
| | | | Median | | Median | |
| [µg/µL] | Conc [M] | nM | Signal | norm. Signal | Signal | norm. Signal |
| 0 | 0.00E+00 | 0.00E+00 | 6459 | 0.00% | 6930 | 0.00% |
| 0.0078 | 3.90E-07 | 3.90E+02 | 5234 | 19.32% | 5309 | 23.81% |
| 0.0156 | 7.80E-07 | 7.80E+02 | 2326 | 65.17% | 3811 | 45.81% |
| 0.03125 | 1.56E-06 | 1.56E+03 | 1644 | 75.92% | 1780 | 75.65% |
| 0.0625 | 3.13E-06 | 3.13E+03 | 921 | 87.32% | 831 | 89.59% |
| 0.125 | 6.25E-06 | 6.25E+03 | 362 | 96.14% | 478 | 94.77% |
| 0.25 | 1.25E-05 | 1.25E+04 | 269 | 97.60% | 281 | 97.66% |
| 0.5 | 2.50E-05 | 2.50E+04 | 182 | 98.98% | 195 | 98.93% |
| | | sec. Ab | 137 | 100.00% | 122 | 100.00% |

FIG. 14

|  | MFI |
|---|---|
| FACS005 | 172 |
| FACS006 | 162 |
| FACS007 | 137 |
| FACS017 | 186 |
| FACS018 | 153 |
| FACS020 | 130 |
| FACS021 | 117 |
| FACS022 | 170 |
| FACS023I | 118 |
| FACS023II | 130 |
| FACS024I | 98.5 |
| FACS024II | 113 |
| FACS024III | 109 |
| FACS024IV | 114 |
| FACS025I | 101 |
| FACS025II | 97.7 |
| FACS026I | 114 |
| FACS026II | 131 |
| FACS027I | 133 |
| FACS027II | 114 |
| FACS027III | 121 |
| FACS027IV | 127 |
| FACS028 | 208 |
| FACS029 | 178 |
| FACS031 | 139 |
| Mean | 134.9 |
| SD | 29 |

FIG. 15

| Test # | FACS | $K_D[10^{-6}M]$ | $IC_{50}$ | cell density |
|---|---|---|---|---|
| 1 | FACS005 | 0.75 | 13.40 | 3.0E+05 |
| 2 | FACS006 | 0.46 | 7.54 | 3.6E+05 |
| 3 | FACS007 | 0.98 | 17.77 | 2.4E+05 |
| 4 | FACS017 | 2.24 | 41.63 | 7.4E+05 |
| 5 | FACS018 | 0.82 | 14.68 | 2.2E+05 |
| 6 | FACS019 | 3.26 | 25.33 | 3.4E+05 |
| 7 | FACS020 | 0.66 | 12.96 | 2.2E+05 |
| 8 | FACS021 | 0.74 | 13.96 | 1.8E+05 |
| 9 | FACS022 | 0.18 | 4.03 | 5.0E+05 |
| 10 | FACS023 | 0.64 | 12.03 | 1.0E+06 |
| 11 | FACS023 | 0.60 | 10.76 | 1.0E+06 |
| 12 | FACS024I | 0.66 | 15.99 | 5.4E+05 |
| 13 | FACS024II | 0.66 | 13.84 | 5.4E+05 |
| 14 | FACS024III | 0.79 | 15.05 | 5.4E+05 |
| 15 | FACS024IV | 0.89 | 16.72 | 5.4E+05 |
| 16 | FACS025I | 0.45 | 12.196 | 5.0E+05 |
| 17 | FACS025II | 0.90 | 14.05 | 5.0E+05 |
| 18 | FACS026 | 0.22 | nD. | 2.6E+05 |
| 19 | FACS027 | 0.34 | 6.84 | 5.2E+05 |
| 20 | FACS028 | 0.15 | 2.61 | 6.6E+05 |
| 21 | FACS029 | 0.20 | 3.82 | 2.4E+05 |
| 22 | FACS031 | 0.29 | 7.72 | 6.0E+05 |
| 23 | FACS032 | 0.32 | 6.75 | 3.0E+05 |
| 24 | FACS034 | 0.32 | 6.42 | 3.4E+05 |
| 25 | FACS039 | 0.24 | 4.85 | 4.0E+05 |

*FIG. 16*

|       | $K_D[10^{-6}M]$ | $IC_{50}$ [μg/mL] |
|-------|-----------------|-------------------|
| Mean  | 0.53            | 10.6              |
| SD    | 0.26            | 4.7               |
| MeanD | 0.25            | 4.1               |

FIG. 17

| Tests | #1-17 | #18-25 |
|-------|-------|--------|
|       | $K_D[10^{-6}M]$ | $IC_{50}$ $IC_{50}$ [μg/mL] |
| Mean  | 0.68  | 0.26   |
| SD    | 0.2   | 0.07   |

FIG. 18

IN VITRO METHOD FOR DETERMINING THE STABILITY OF COMPOSITIONS COMPRISING SOLUBLE FC GAMMA RECEPTOR(S)

The present invention relates in essence to an in vitro method for determining the stability of a composition which comprises or essentially consists of soluble human Fc gamma receptor IIA, IIB, IIIA and/or IIIB, said method comprising the steps of contacting a surface comprising human Fc gamma receptor IIA, IIB, IIIA and/or IIIB with a set amount of aggregated human IgG; contacting said surface comprising human Fc gamma receptor IIA, IIB, IIIA and/or IIIB with a set amount of said composition of soluble human Fc gamma receptor IIA, IIB, IIIA and/or IIIB; determining the amount of aggregated human IgG which is bound to said surface comprising said human Fc gamma receptor IIA, IIB, IIIA and/or IIIB, and comparing the amount of aggregated human IgG which is bound to said surface as determined in step (c) with a reference value and (thereby) determining the stability of said composition which comprises or essentially consists of soluble human Fc gamma receptor IIA, IIB, IIIA and/or IIIB. The present invention also relates to aggregated human IgG obtainable by a method as defined herein, as well as to the use of the mentioned aggregated human IgG in the methods of the invention.

Fc receptors (FcRs) play a central role in the immune system where they control the extent and strength of an immune response. After pathogens have gained access to the blood circulation they are opsonized by immunoglobulins (Igs). The resulting immunocomplexes (ICs) bind due to their multivalency with high avidity to FcR bearing cells leading to clustering of the FcRs, which triggers several effector functions (Metzger, H., J. Immunol. 1992, 149: 1477-1487). These include, depending on the expressed FcR type and associated proteins, endocytosis with subsequent neutralization of the pathogens and antigen presentation, antibody-dependent cellular cytotoxity (ADCC), secretion of mediators or the regulation of antibody production (Fridman et al, Immunol. Rev. 1992, 125:49-76; van de Winkel and Capel, Immunol. Today 1993, 14:215-221).

Immune complexes derive from complex interactions between antibody, antigens, complement and various receptors as a part of adaptive immunity. Antigens bound to antibodies in immune complexes are normally cleared by various cellular mechanisms physiologically capable of eliminating even small quantities of 'foreign' antigens from circulation. Immune complexes can form when humans are exposed to foreign substances like proteins (infections, vaccines, drugs, etc.) or nonprotein materials (haptens) which need a protein carrier to activate the cascade. Autoimmune disorders develop when (pathogenic) immune complexes deposit pathologically in different organs, initiating inflammatory cascades which lead to organ damage/disease. Immune complex disease can manifest in a myriad of ways when dysregulation in one or more of these components occur.

Specific FcRs exist for all immunoglobulin (Ig) classes. As IgG is the most abundant antibody isotype found in the human circulation, it follows that the FcRs for IgG, Fc gamma receptors (FcγRs), are the most abundant with the widest diversity. Orthologous proteins corresponding to the human FcγRs are found in other mammalian species, including other primates such as monkeys and mice. Like humans, other species have several FcγRs with varying affinity for their corresponding IgG subclasses. The FcγRs comprise both activating and inhibitory receptors, and this integration of positive and negative signals is necessary for a productive immune response.

Three classes of FcγRs exist in humans: the high affinity receptor FcγRI and the low affinity receptors FcγRII and FcγRII. FcγRI (CD64), FcγRII (CD32) and FcγRIIIA (CD16) occur as type I transmembrane proteins or in soluble forms (sFcRs) but a glycosylphosphatidylinositol anchored form of the FcγRIII (FcγRIIIB) also exists. Furthermore, FcγRs occur in various isoforms (FcγRIA, B1, B2, C; FcγRIIA1-2, B1-3, C) and alleles (FcγRIIa1-HR, -LR; FcγRIIIb-NA1, -NA2) (van de Winkel and Capel, Immunol. Today 1993, 14:215-221). As mentioned above, these FcγRs have different affinity to IgG and specifically different binding affinity to the different IgG subclasses. There are four IgG subclasses in humans, named in order of their abundance in the serum (IgG1 (66%), 2 (23%), 3 (7%), and 4 (4%); Hashira et al., Pediatr. Int. 2000, 42(4):337-342).

FcγRII is the receptor with the widest distribution on immunocompetent cells and, together with FcγRIIIA is mainly involved in the endocytosis of immune complexes. FcγRII exists in three isoforms, FcγRIIA, FcγRIIB and FcγRIIC, however the extracellular region of FcγRIIB and FcγRIIC are identical whereas FcγRIIA differs in its extracellular region by only 7% of the amino acid residues. Nevertheless, both forms can be distinguished by their binding characteristics to human and mouse IgG subclasses (van de Winkel and Capel, Immunol. Today 1993, 14:215-221) and their differing affinity to human IgGs (Bruhns et al., Blood 2009, 113:3716-3725). FcγRIIIA is the key receptor for the induction of ADCC, while the inhibitory FcγRIIB represents the sole FcγR, which is expressed on B cells. There, the expression of FcγRIIB is essential for the down regulation of B cells resulting in a reduction of antibody production.

Based on sFcγRIIB, the inventors are developing novel means and methods for the treatment of autoimmune diseases. The most advanced product is SM101, which competes with FcγRs expressed on immune cells for the binding of pathogenic immune complexes. SM101 is currently involved in clinical trials in the US and Europe for the treatment of autoimmune disorders such as Lupus Erythematosus and Immune Thrombocytopenia.

It is assumed that proteinaceous medicaments, e.g. a medicament or pharmaceutical composition comprising SM101, may degrade during storage and it is therefore highly desirable to develop reproducible in vitro tests that reflect the residual activity of such proteins or compositions comprising them.

Thus the technical problem of the present invention was to develop an in vitro method for determining the stability of compositions comprising soluble human FcγRs.

To present inventors observed that human IgG preparations obtained from a collective of "normal" or "healthy" persons (for example commercially available Intravenous Immunoglobulin (IVIG) preparations) comprise a so far unidentified fraction of aggregated human IgG which can be provided in a standardized and reliable fashion. This is surprising, as it was not known before that such analogues of pathogenic immune complexes can be derived from an otherwise "normal" or healthy" collective of human beings. Said aggregated human IgG binds to FcγR receptors and thereby mimics the in vivo situation (i.e. it mimics the aforementioned pathogenic immune complexes) and can thus be used in methods which aim to detect, determine or verify the stability of compositions comprising soluble human Fc gamma receptor IIA, IIB, IIIA and/or IIIB.

Notably, the aggregated human IgG is not heat aggregated as, for example, described in Engelhard, et al., (1990), Eur. J. Immunol. 20, 1367-1377, Bruhns et al. (2009), Blood J. 113(16), 3716-3725 or US 2008/008700. Bruhns et al. describe heat-aggregated human IgG (page 3718, Immunoglobulin binding assays), that are generated by incubation of human IgG in a borate-buffered saline solution at pH 8.0 and 63° C. for 30 minutes without any subsequent treatment and artificial immune complexes derived from chemically modified BSA (NIP12-BSA-biotin) in complex with anti-NIP mAbs purified from cell culture supernatants (page 3717, Antibodies and reagents). Likewise, US 2008/008700 discloses the use of HAGG (heat-aggregated IgG) on page 8, [0093].

The present invention consequently relates to an in vitro method for determining the stability (such as the shelf stability or storage stability) of a composition, preferably of a pharmaceutical composition (equating with a medicament), which composition comprises or essentially consists of soluble human Fc gamma receptor IIA, IIB, IIIA and/or IIIB, said method comprising the steps of:

(a) contacting a surface comprising human Fc gamma receptor IIA, IIB, IIIA and/or IIIB with a set amount of aggregated human IgG;
(b) contacting said surface comprising human Fc gamma receptor IIA, IIB, IIIA and/or IIIB with a set amount of said composition of soluble human Fc gamma receptor IIA, IIB, IIIA and/or IIIB; and
(c) determining the amount of aggregated human IgG which is bound to said surface comprising said human Fc gamma receptor IIA, IIB, IIIA and/or IIIB,
(d) and comparing the amount of aggregated human IgG which is bound to said surface as determined in step (c) with a reference value and (thereby) determining the stability such as the shelf stability; stability over time; shelf life of said composition which comprises or essentially consists of soluble human Fc gamma receptor IIA, IIB, IIIA and/or IIIB.

Steps (a) and (b) of the methods of the invention can be carried out concomitantly or consecutively. It is also envisaged that the order of steps (b) and (a) is reversed.

It is envisaged that the methods of the invention comprise a washing step which is to be conducted prior to step (c) and preferably after step (a) and (b).

It is preferred that said soluble human Fc gamma receptor which is employed in the context of the present invention is a soluble Fc gamma IIB receptor. It is particularly preferred that said soluble human Fc gamma IIB receptor is SM101 (SEQ ID No. 1), including preparations of these receptors that can be obtained via expression of these receptors in host cells, such as for example mammalian cells or bacterial cells like *E. coli*.

The present invention likewise relates to the use of the aggregated human IgG that is defined herein, in the methods and embodiments of the present invention.

In the context of the present invention, the term "in vitro method" refers to a method that is performed outside of the human or animal body, in contrast to an in vivo method.

The word "method" can be replaced with "test" or "assay" or the like.

The term "stability" comprises the "shelf stability" or "shelf life" or "half-life". The "stability" of a composition relates in essence to the stability of the main ingredient contained therein, i.e. the stability of the soluble human Fc gamma receptor IIA, IIB, IIIA and/or IIIB defined herein. Said stability might be affected by different parameters, such as time, i.e. "stability over time"; temperature, buffer conditions, production host of the soluble human Fc gamma receptor IIA, IIB, IIIA and/or IIIB; sequence of the human Fc gamma receptor IIA, IIB, IIIA and/or IIIB; method of manufacture of the human Fc gamma receptor IIA, IIB, IIIA and/or IIIB etc.

By determining the stability of the composition of the invention (which comprises or essentially consists of soluble human Fc gamma receptor IIA, IIB, IIIA and/or IIIB) it is likewise possible to monitor/control the quality/condition/binding capacity of said composition (i.e. in essence of the main ingredient of said composition which is the soluble human Fc gamma receptor IIA, IIB, IIIA and/or IIIB).

The "composition" is in a preferred embodiment a pharmaceutical composition (which equates with a medicament) or a diagnostic composition, and may comprise additionally pharmaceutically or diagnostically acceptable carriers, buffers, ingredients etc. Said composition may also comprise further therapeutically active ingredients.

The term "aggregated human IgG" (sometimes also denoted as "human aggregated IgG" or the like) refers to the aggregated portion of a human IgG preparation. Such preparations are surprisingly present in blood-based products (such as pooled human IgG preparations or IVIGs) that may be used for intravenous or subcutan or muscular administration, which products contain pooled (preferably polyvalent) IgG. Thus, aggregated human IgG can preferably be obtained/isolated or is obtainable from pooled human IgG preparations, such as IVIG preparations/compositions. It is envisaged that said aggregated human IgG is an aggregated human IgG that can be isolated from "human protein" that is characterized by a content of at least 90% human IgG. Said human protein is derived/derivable from human serum or plasma and is in a preferred embodiment characterized or identified as normal human immunoglobulin (human IgG) with the ATC-code J06BA01 or J06BA02 in accordance with the Anatomical Therapeutic Chemical (ATC) classification system of the WHO Collaborating Centre for Drug Statistics Methodology (WHOCC). The term "human protein" when used herein includes pooled human IgG preparations. In a preferred embodiment, the human IgG comprises at least 50% IgG of the subtype IgG1. In a more preferred embodiment, the human IgG (further) comprises at least 20% IgG of the subtype IgG2. In a particularly preferred embodiment, said aggregated human IgG is obtained/isolated or obtainable from BERIGLOBIN™, VARITECT™ or VENBIG™, BERIGLOBIN™ being preferred. BERIGLOBIN™ comprises 95% or more, such as 100% IgG. For example, a 100% IgG containing Beriglobin can comprise 61% IgG1, 28% IgG2, 5% IgG3, 6% IgG4 and may at a maximum comprise about 1% IgA. Percent values indicated for BERIGLOBIN™, VARITECT™ and VENBIG™ refer to % (w/w). An exemplary BERIGLOBIN™ is the one with batch number 26840311A or 23840311B. VARITECT™ comprises 95% or more, such as 100% IgG. For example, a 100% IgG VARITECT™ can comprise 59% IgG1, 36% IgG2, 3% IgG3, 2% IgG4, and may comprises 5% or less IgA. VENBIG™ comprises 95% or more, such as 100% IgG. For example, a 100% IgG VENBIG™ can comprise 52-80% IgG1, 26-50% IgG2, 2.4-5% IgG3, 0.3-1% IgG4. Of course, the skilled person can apply BERIGLOBIN™ VARITECT™, VENBIG™ or any other Composition like these three medicaments in the methods and uses of the present invention. Another preferred aggregated human IgG is obtained/isolated or obtainable from SUBCUVIA™. For example, a 100% IgG SUBCUVIA™ can comprise 45-75% IgG1, 20-45% IgG2, 3-10% IgG3, 2-8% IgG4. Percent values indicated for SUBCUVIA™ refer to % (w/w). An exemplary SUBCUVIA™ is the one with batch number BVNG1M032A.

However, the skilled person can not only use these three medicaments, but can also prepare a human IgG preparation by himself. Indeed, the skilled person is readily in a position to prepare an IgG preparation as described herein, for example, by pooling IgG from plasma of at least 100, 200, 300, 400, 500, 600, 700, 800, 900, or more, preferably 1000 or more human donors, thereby a (pooled) human IgG preparation is obtained. As a result, a human IgG preparation as applied in the present invention comprises preferably 95% or more, such as 100% IgG. An IgG preparation as applied herein preferably comprises IgG subclasses as follows: 52-80% (w/w) IgG1, 26-50% IgG2 (w/w), 2-5% IgG3 (w/w), and/or 0.2-6% (w/w) IgG4, with the proviso that the total IgG content does not exceed 100% (w/w).

In a further preferred embodiment, said human protein consists of or comprises mixed serum or plasma from at least 100, i.e. 100, 200, 300, 400, 500, 600, 700, 800, 900, 1000 etc. human (healthy or "standard") donors, comprising all four IgG subgroups. Mixed serum or plasma from at least 500 human (healthy or "standard") donors is preferred. The term "healthy" means an individual who meets the current (at the time of donation) standard eligibility criteria for donating blood, bearing in mind that such eligibility criteria are subject to continuous improvement and change.

In another embodiment, it is envisaged that said aggregated human IgG is an aggregated human IgG that is obtainable from said human protein by an isolation method comprising size exclusion chromatography. In a preferred embodiment, said size exclusion chromatography separates monomeric and/or dimeric IgG from said aggregated human IgG. Means and methods to isolate the aggregated human IgG that can be used in the context of the present invention are disclosed herein elsewhere (e.g. in the Examples). It is also envisaged that the aggregated human IgG of the present invention is not heat aggregated human IgG like for example the one described in Engelhard, et al., (1990), Eur. J. Immunol. 20, 1367-1377, Bruhns et al. (2009), Blood J. 113(16), 3716-3725 or US 2008/008700. Indeed, heat aggregated IgG will differ from aggregated IgG as is obtained/is obtainable as described herein. Namely, heat aggregation is a result of the partial denaturation of proteins when temperatures above the melting temperature (Tm) are applied to a given protein. The melting temperature is a function of the protein and in case of a mixture of human IgGs a broad range of Tm will necessarily be observed. Thus the degree of aggregation will vary from one batch to the other depending on the mixture of IgG used.

Moreover, a number of monomeric IgG will inevitably be part of the preparation of aggregated IgG by heat and thus would not allow a preparation of aggregated IgG without varying amounts of monomeric IgG considered to be impurities. However, the methods for the preparation of aggregated IgG as described herein separate monomeric and/or dimeric IgG from aggregated IgG and, thus, the resulting aggregated IgG as is obtained/is obtainable by the methods described herein is different from heat-aggregated IgG from the prior art.

It is thus apparent that heat aggregated IgG is not comparable to the aggregated IgG preparations as disclosed by the present invention, which offer long-term stability and are perfectly suited for batch release testing or other routine testing.

It is envisaged that pooled human IgG preparations such as Intravenous immunoglobulin (IVIG) preparations, sometimes also called plasma immunoglobulin for intravenous administration, are derived from pooled plasma of hundreds of healthy donors and contain both immune and natural antibodies (NAbs) reflecting the cumulative antigen experience of the donor population. A pooled human IgG preparation is by its nature highly polyclonal and contains many antibody species. It thus contains a large spectrum of so-called "immune antibodies" with specificities directed against pathogens and foreign antigens as well as NAbs reacting with a broad range of antigens including self/autoantigens. NAbs are so defined as they are generated in the absence of deliberate immunization and independently of exposure to foreign antigens.

In addition to intravenous preparations there are preparations designed for subcutaneous (SCIG) and intramuscular (IMIG) administration. As used herein the term "IVIG" is intended to encompass IVIG, SCIG and IMIG preparations. IVIG formulations are well known and include INTRAGAM® P, PRIVIGEN®, HIZENTRA®, GAMUNEX®, FLEBOGAMMA®, OCTAGAM® and GAMIMUNE®.

One feature shared by pooled human IgG preparations, such as IVIG preparations is that as they are derived from normal plasma or serum the major immunoglobulin species they contain is IgG for example at least 98% of the immunoglobulin in INTRAGAM™ P and PRIVIGEN® is IgG. Accordingly, a pooled human IgG preparation such as an IVIG can be viewed as a concentrated preparation of IgG.

In preferred embodiments the IVIG contains at least 5% w/v, at least 10% w/v, at least 20% w/v or at least 25% immunoglobulin.

Examples of IVIG preparations are given in WO 2005/023867 in Table 1. All of these examples are preferred IVIG preparations that can be applied in the context of the present invention.

The aggregated human IgG defined herein is optionally labeled, and the label is either directly or indirectly connected with the aggregated human IgG. "Directly" thereby means a covalently linked label (which may also comprise a linker) while indirectly includes the binding of the aggregated human IgG by a labeled second entity that binds to the aggregated human IgG, e.g. a labeled binding domain such as an antibody or fragments thereof (e.g. anti-human antibodies such as a labeled secondary anti-human IgG antibody). The secondary labeled antibody can be any anti-IgG antibody available, in the examples below, goat anti-human IgG labeled with R-Phycoerythrin (Dianova, Cat. No 109-116-088) was used, however many other antibodies are commercially available that would be equally suitable. Inter alia "fluorescent labels" are envisaged in the context of the present invention, but the present invention is not limited thereto, i.e. other labels are likewise envisaged (for example labels that can be employed in immunological methods such as ELISA methods). The fluorescent label are preferably selected from the group comprising quantum dot agents, fluorescent proteins, fluorescent dyes, pH-sensitive fluorescent dyes, voltage sensitive fluorescent dyes and/or fluorescent labeled microspheres. Fluorescent label being excitable with a laser beam and emitting light at a set wave length being detectable by means of a FACS apparatus are preferred.

For the experiments that led to the present invention, the commercial product BERIGLOBIN™ was used and the aggregated human IgG was separated out from monomeric and dimeric IgG by preparative Size Exclusion Chromatography (SEC) (see detailed description below and example 2). However, any other "human protein" as described herein could be used as a starting point for the isolation of aggregated human IgG, e.g. BERIGLOBIN™, VARITECT™ and VENBIG™ are suitable products currently on the German Market or a IgG preparation as described herein, for example, by pooling IgG from plasma of at least 100, 200, 300, 400, 500 or more, preferably 1000 or more human donors. Any of these "starting points" (including human protein as defined herein, (pooled) IgG preparations, such as IVIGs) can be used for the isolation of aggregated human IgG by, e.g., the preparative Size Exclusion Chromatography (SEC) (see detailed description below and example 2). The U.S. FDA has 10 products listed at present. The use of a "human protein", e.g. BERIGLOBIN™ as raw material is particularly preferred, as this provides for a controlled source for the aggregated human IgG product to be used as a standard in the embodiments of the invention. The aggregated human IgG can be adjusted to have a protein content of between 0.35 mg/mL and 1.40 mg/mL, preferably between 0.5 and 1.35 mg/ML. The skilled person will be aware that the protein content can be adjusted by diluting with a suitable buffer or concentrated, for example by ultrafiltration. Further guidance is provided in Examples 1 and 2 of the present invention.

In the last step of the method for determining the stability of a composition which comprises or essentially consists of soluble human Fc gamma receptor IIa, IIB, IIIA and/or IIIB the amount of aggregated human IgG which is bound by to the surface and which is determined as described herein is compared with a reference value. Said comparing step allows the determination of the stability of said composition as follows.

For example, the higher the stability of a composition whose stability is determined in comparison to a composition also comprising Fc gamma receptors, the less aggregated IgG will bind to the surface comprising human Fc gamma receptor IIA, IIB, IIIA and/or IIIB, since it will be bound by one or more soluble human Fc gamma receptors comprised by said composition.

On the other hand, for example, the more aggregated IgG will bind to the surface comprising human Fc gamma receptor IIA, IIB, IIIA and/or IIIB, the less stable is the composition in comparison to a composition also comprising Fc gamma receptors like the composition whose stability is determined in accordance with the methods described herein. However, "less stable" does not mean that the composition whose stability is determined is not valuable. On the contrary, for certain applications it may be desirable to have a composition that is, for example, less stable than a reference composition, since it may be desirable to have a composition whose ingredients have a shortened half-life, less pH stability, etc.

As said, a reference composition also comprises one or more of the human Fc gamma receptor(s) like the composition whose stability is determined in accordance with the methods of the present invention is referred to herein as reference composition.

For said reference composition, the value reflecting the amount of aggregated human IgG which is bound to a surface was determined as described herein such that said value is available as a reference value. Hence, the reference value is determined and is thus available before the stability of a composition is determined in accordance with the teaching of the present invention. Accordingly, said reference value can then be compared with the amount of aggregated human IgG which is bound to a surface as determined as described herein, which amount is then converted into a value that is compared with a reference value. By that comparison, it is possible to determine the stability of a composition. In fact, as explained a reference value was determined and said reference value reflects a certain amount of aggregated human IgG bound by a surface. Hence, the reference value indirectly reflects the amount of IgG bound by one or more soluble human Fc receptors comprised by said composition.

Of course, a reference composition is only then comparable with a composition whose stability is determined in accordance with the embodiments of the present invention, if it comprises that same one or more soluble Fc gamma receptors in a comparable amount (ideally the same amount).

A reference value can reflect the stability of a composition as described herein, for example, as regards, temperature stability, pH stability, storage buffer stability, shelf stability, shelf life, half-life, stability (or resistance) against degradation, stability regarding the monomeric form, etc. of the Fc gamma receptors as described herein. However, it is not decisive which stability property or stability parameter of the composition is determined, since this can depend, for example, on the demands and/or interests and/or the purpose for which the composition may be used.

In fact, the methods of the present invention are not limited to the testing of any specific parameter that may influence stability, since the methods of the present invention allow a general read-out of the stability of a composition, because it is always the amount of aggregated human IgG that is bound to a surface as described herein that is determined or, in the alternative, the amount of aggregated human IgG that is bound by one or more soluble human Fc gamma receptors comprised by a composition whose stability is determined in accordance with the teaching of the present invention.

As explained above, the less aggregated IgG is bound to a surface, the more potent or still potent is the one or more soluble human Fc gamma receptors comprised by said composition. For example, when being interested in the pH stability of a composition, the skilled person can subject such a composition to various pH conditions and then test the bound aggregated human IgG to a surface while being in contact with said composition. Assuming that said composition is stable, for example, against an acidic pH, the one or more soluble human Fc gamma receptor will still be able to bind aggregated human IgG and thus less aggregated IgG will bind to a surface as described herein. Of course, the skilled person knows that he may have to apply a suitable buffer after having tested pH stability when performing the methods of the present invention. For example, a too acidic or basic environment could disturb the methods described herein and, thus, prior to applying them, the skilled person may have to adjust or adapt the buffering conditions by means and methods commonly known in the art.

By way of another example, if one is interested in a composition that has a long shelf-life or resistance against degradation, he uses that composition as reference composition and determines the amount of aggregated IgG bound to a surface as described herein after he has stored the composition, for example, for one, two, six or twelve months and uses that value as reference value for the desired property of the composition. Thereafter, said reference value that reflects, for example, long shelf-life or resistance against degradation will be compared with the value reflecting the amount of aggregated human IgG being bound to a surface as described herein when also being contacted with the composition whose stability is determined by the methods of the present invention.

A reference value that is, for example, determined after twelve months storage and that is regarded as meeting the expectations of the practitioner can be set to be, for example, 100, with 100 being a relative value, since it merely reflects a certain amount of aggregated human IgG bound to a surface.

A reference value is regarded as acceptable if at least 50%, preferably 60% or 70%, more preferably 80% or 90% of the aggregated human IgG is not bound to a surface, but is bound by one or more soluble human Fc gamma receptors comprised by the composition whose stability is determined. Specifically, as explained above, the less aggregated human IgG is bound to a surface, the more is bound by one or more soluble Fc gamma receptors and vice versa. Accordingly, the higher the stability of a composition, the less aggregated human IgG will be bound by a surface, but by one or more soluble human Fc gamma receptors. Conversely, the lesser the stability of a composition, the more aggregated human IgG will be bound by a surface, and the less will be bound by one or more soluble human Fc gamma receptors The present invention also encompasses a method for isolating aggregated human IgG from the mixed plasma of at least 500 (healthy or "standard") donors by size exclusion chromatography.

It is also envisaged that the aggregated human IgG of the invention is supplemented or replaced by the corresponding IgG preparations of non-human primates, such as cynomolgous, callithrix, macaqua, *sanguis* or the like.

The "soluble human FcγRIIA, FcγRIIB, FcγRIIIA or FcγRIIIB" of the invention are for example those described in EP 1 135 486 and EP 1 642 974 and EP 1 446 139. The "soluble human FcγRIIA, FcγRIIB, FcγRIIIA or FcγRIIIB" of the invention are in a preferred embodiment characterized by the absence of transmembrane domains and signal peptides. The claimed soluble FcγRs of the invention comprise or consist in a preferred embodiment of an amino acid sequence corresponding to that of SEQ ID NO.: 1 (SM101, recombinant human FcγRIIB), SEQ ID NO.: 3 (FcγRIIB), SEQ ID NO.: 5 (FcγRIIA), SEQ ID NO.: 7 (FcγRIIIA) or SEQ ID NO.: 9 (FcγRIIIB) encoded by the respective nucleic acid sequences SEQ ID NO.: 2, 4, 6, 8, and 10. The invention also encompasses soluble FcγRs that have at least 90%, preferably 95% identity to the proteins of SEQ ID Nos.: 1, 3, 5, 7, or 9. For the determination of sequence identity a comparison is made by aligning the sequences in a manner to provide the maximum correspondence of amino acids. In a preferred embodiment of the invention, the soluble human Fc gamma receptor is FcγRIB (SEQ ID NO.: 3). In a more preferred embodiment, the soluble human receptor is SM101 (SEQ ID NO.:1), which is a soluble FcγRIIB receptor. In a further preferred embodiment of the methods of the invention, only one soluble receptor (or as mentioned above a mixture of proteins all having at least 90% identity to the receptor of interest) should be tested at a time.

The sequences that the present application refers to are depicted below.

```
(SM101)
                                                         SEQ ID No. 1
MAPPKAVLKL EPQWINVLQE DSVTLTCRGT HSPESDSIQW FHNGNLIPTH

TQPSYRFKAN NNDSGEYTCQ TGQTSLSDPV HLTVLSEWLV LQTPHLEFQE

GETIVLRCHS WKDKPLVKVT FFQNGKSKKF SRSDPNFSIP QANHSHSGDY

HCTGNIGYTL YSSKPVTITV QAPSSSP (SM101, cDNA)
                                                         SEQ ID No. 2
    1  ATGGCACCGC CGAAAGCAGT TCTGAAACTG GAACCGCAGT GGATTAACGT TCTGCAGGAA

61  GATAGCGTTA CCCTGACCTG TCGTGGCACC CATAGCCCGG AAAGCGATAG CATTCAGTGG

121  TTTCACAACG GCAATCTGAT TCCGACCCAT ACCCAGCCGA GCTATCGTTT TAAAGCGAAC

181  AACAACGATA GCGGCGAATA TACCTGTCAG ACCGGTCAGA CCAGCCTGAG CGATCCGGTT

241  CATCTGACCG TTCTGAGCGA ATGGCTGGTT CTGCAGACCC CGCATCTGGA ATTTCAGGAA

301  GGCGAAACCA TTGTTCTGCG TTGCCACAGC TGGAAAGATA AACCGCTGGT TAAAGTTACC

361  TTCTTCCAGA ACGGCAAAAG CAAAAAATTC AGCCGTAGCG ATCCGAATTT TAGCATTCCG

421  CAGGCGAATC ATAGCCATAG CGGCGATTAT CATTGTACCG GCAACATTGG CTATACCCTG

481  TATAGCAGCA AACCGGTGAC CATTACCGTT CAGGCGCCGA GCAGCAGCCC GTAA (human FcγRIIB)
                                                         SEQ ID No. 3
MGTPAAPPKA VLKLEPQWIN VLQEDSVTLT CRGTHSPESD SIQWFHNGNL IPTHTQPSYR

FKANNNDSGE YTCQTGQTSL SDPVHLTVLS EWLVLQTPHL EFQEGETIVL RCHSWKDKPL

VKVTFFQNGK SKKFSRSDPN FSIPQANHSH SGDYHCTGNI GYTLYSSKPV TITVQAPSSS

P (human FcγRIIB, cDNA)
                                                         SEQ ID No. 4
    1  atggggacac ctgcagctcc cccaaaggct gtgctgaaac tcgagcccca gtggatcaac 61  gtgctccagg aggactctgt gactctgaca tgccggggga ctcacagccc tgagagcgac
```

```
121  tccattcagt ggttccacaa tgggaatctc attcccaccc acacgcagcc cagctacagg
181  ttcaaggcca acaacaatga cagcggggag tacacgtgcc agactggcca gaccagcctc
241  agcgaccctg tgcatctgac tgtgctttct gagtggctgg tgctccagac ccctcacctg
301  gagttccagg agggagaaac catcgtgctg aggtgccaca gctggaagga caagcctctg
361  gtcaaggtca cattcttcca gaatggaaaa tccagaaat tttcccgttc ggatcccaac
421  ttctccatcc cacaagcaaa ccacagtcac agtggtgatt accctgcac aggaaacata
481  ggctacacgc tgtactcatc caagcctgtg accatcactg tccaagctcc cagctcttca
541  ccg
```

(human FcγRIIA)                                                    SEQ ID No. 5

MGTPAAPPKA VLKLEPPWIN VLQEDSVTLT CQGARSPESD SIQWFHNGNL IPTHTQPSYR
FKANNNDSGE YTCQTGQTSL SDPVHLTVLS EWLVLQTPHL EFQEGETIML RCHSWKDKPL
VKVTFFQNGK SQKFSHLDPT FSIPQANHSH SGDYHCTGNI GYTLFSSKPV TITVQVPSMG
SSSP (human FcγRIIA, cDNA)                                              SEQ ID No. 6
```
  1  atggggacac ctgcagctcc cccaaaggct gtgctgaaac ttgagccccc gtggatcaac
 61  gtgctccagg aggactctgt gactctgaca tgccaggggg ctcgcagccc tgagagcgac
121  tccattcagt ggttccacaa tgggaatctc attcccaccc acacgcagcc cagctacagg
181  ttcaaggcca acaacaatga cagcggggag tacacgtgcc agactggcca gaccagcctc
241  agcgaccctg tgcatctgac tgtgctttcc gaatggctgg tgctccagac ccctcacctg
301  gagttccagg agggagaaac catcatgctg aggtgccaca gctggaagga caagcctctg
361  gtcaaggtca cattcttcca gaatggaaaa tccagaaat tctcccatt ggatcccacc
421  ttctccatcc cacaagcaaa ccacagtcac agtggtgatt accactgcac aggaaacata
481  ggctacacgc tgttctcatc caagcctgtg accatcactg tccaagtgcc cagcatgggc
541  agctcttcac caat
```

(human FcγRIIIA)                                                   SEQ ID No. 7

MDLPKAVVFL EPQWYRVLEK DSVTLKCQGA YSPEDNSTQWF HNESLISSQA SSYFIDAATV
DDSGEYRCQ TNLSTLSDPV QLEVHIGWLL LQAPRWVFKEE DPIHLRCHSW KNTALHKVTY
LQNGKGRKY FHHNSDFYIP KATLKDSGSY FCRGLVGSKNV SSETVNITIT QGLSVSTISS
F (human FcγRIIIA, cDNA)                                             SEQ ID No. 8
```
  1  atggatctcccaa aggctgtggt gttcctggag cctcaatggt acagggtgct cgagaaggac
 61  agtgtgactc tgaagtgcca gggagcctac tcccctgagg acaattccac acagtggttt
121  cacaatgaga gcctcatctc aagccaggcc tcgagctact tcattgacgc tgccacagtt
181  gacgacagtg gagagtacag gtgccagaca aacctctcca ccctcagtga cccggtgcag
241  ctagaagtcc atatcggctg gctgttgctc aggcccctc ggtgggtgtt caaggaggaa
301  gaccctattc acctgaggtg tcacagctgg aagaacactg ctctgcataa ggtcacatat
361  ttacagaatg gcaaaggcag gaagtatttt catcataatt ctgacttcta cattccaaaa
421  gccacactca agacagcgg ctcctacttc tgcaggggc ttgttgggag taaaaatgtg
481  tcttcagaga ctgtgaacat caccatcact caaggtttgt cagtgtcaac catctcatca
541  ttc
```

-continued (human FcγRIIIB)

SEQ ID No. 9

MDLPKAVVFLE PQWYSVLEKD SVTLKCQGAY SPEDNSTQWF HNENLISSQA SSYFIDAATV

NDSGEYRCQT NLSTLSDPVQ LEVHIGWLLL QAPRWVFKEE DPIHLRCHSW KNTALHKVTY

LQNGKDRKYF HHNSDFHIPK ATLKDSGSYF CRGLVGSKNV SSETVNITIT QGLAVSTISS

F (human FcγRIIIB, cDNA)

SEQ ID No. 10

```
  1  atggatctcc caaaggctgt ggtgttcctg gagcctcaat ggtacagcgt gcttgagaag 61  gacagtgtga ctctgaagtg ccagggagcc tactcccctg aggacaattc cacacagtgg 121  tttcacaatg agaacctcat ctcaagccag gcctcgagct acttcattga cgctgccaca 181  gtcaacgaca gtggagagta caggtgccag acaaacctct ccaccctcag tgacccggtg 241  cagctagaag tccatatcgg ctggctgttg ctccaggccc ctcggtgggt gttcaaggag 301  gaagaccccta ttcacctgag gtgtcacagc tggaagaaca ctgctctgca taaggtcaca 361  tatttacaga atggcaaaga caggaagtat tttcatcata attctgactt ccacattcca 421  aaagccacac tcaaagatag cggctcctac ttctgcaggg ggcttgttgg gagtaaaaat 481  gtgtcttcag agactgtgaa catcaccatc actcaaggtt tggcagtgtc aaccatctca 541  tcattc
```

While the embodiments of the invention are directed to human FcγRs, they could also be applied to other mammalian FcγRs, specifically to those from mice or primates such as monkeys.

The "surface comprising human Fc gamma receptor IIA, IIB, IIIA and/or IIIB" is or comprises in some embodiments a cell or cell line, preferably a mammalian cell or a mammalian cell line expressing one or more human Fc gamma receptor IIA, IIB, IIIA and/or IIIB. These cells express in some embodiments the human Fc gamma receptor IIA, IIB, IIIA or IIIB in the absence of any other human Fc gamma receptor, i.e. these cells/cell lines only express one FcγR. It is particularly preferred that said surface comprising human Fc gamma receptor IIA, IIB, IIIA and/or IIIB, comprises in essence or even exclusively human FcγRIIB. In a further preferred embodiment, the subtype of the human Fc gamma receptor comprised by said surface and the subtype of the human Fc gamma receptor comprised by said composition of soluble human Fc gamma receptor is identical. When FcγRIIB is being tested, the cells preferably express only FcγRIIB, such as the Raji lymphoblastoid cell line (CCL-86, ATCC). For FcγRIIA, the erythroleukemic cell line K562 (CCL-243, ATCC) can be used, and for FcγRIIIA the NKL cell line (Robertson et al., Exp. Haematol. 1996, 24(3):406-15) can be used. Alternately, CHO cells transfected with the FcR(s) of interest can be used. Methods for the transfection of CHO cells to express a protein of interest are well known in the art, this method is described for example in Bruhns et al., Blood 2009, 113:3716-3725

It is also envisaged that the "surface comprising human Fc gamma receptor IIA, IIB, IIIA and/or IIIB" is or comprises a solid surface that can be coated with human Fc gamma receptor IIA, IIB, IIIA and/or IIIB. A "solid surface" thereby comprises either a particulate material (beads) which e.g. may be magnetically attractable or a flat surface such as an ELISA plate or a Biacore detection unit. The material of said surface may be any suitable solid material such as plastic, polymers, metal, glass etc. that can be employed in the respective methods. The coating of proteins like human Fc gamma receptor IIA, IIB, IIIA and/or IIIB to a solid surface (e.g. a flat surface or a particulate surface) is conducted by standard methods which are well known to the skilled person. The coating of a solid surface may be conducted with "human FcγRIIA, FcγRIIB, FcγRIIIA or FcγRIIIB" and/or with "soluble human FcγRIIA, FcγRIIB, FcγRIIIA or FcγRIIIB" of the invention, as there is no need of biological expression on the cell surface (which would require a membrane anchor).

In a preferred embodiment, the invention relies on the use of aggregated human IgG in an in vitro method for determining the binding activity of soluble human Fc gamma receptors. The first step in the method of the invention comprises contacting a mammalian cell from a cell line expressing only one of the human Fc gamma receptors IIA, IIB, IIIA or IIIB (preferably in the absence of any other Fcγreceptor) with a set amount of aggregated human IgG and a set amount of the corresponding soluble human Fc gamma receptor IIA, IIB IIIA or IIIB. It is preferred that the mammalian cells chosen for the first step of the method express only the Fc gamma receptor of interest and if possible no other Fc gamma receptors, as the presence of further receptors that bind to IgG could interfere with the activity of the soluble FcγR being tested.

"Determining the amount of aggregated human IgG which is bound to said surface" refers to the measurement or quantification of the amount of aggregated human IgG bound to the surface, i.e. what is preferably measured in the context of the present invention is the amount of aggregated human IgG which is bound to the surface comprising human Fc gamma receptor IIA, IIB, IIIA and/or IIIB. Said bound aggregated human IgG is for example detected by means of an indirect label (e.g. an anti-human IgG binding domain) or by means of a direct label (i.e. the aggregated human IgG is labeled directly—explained herein elsewhere). For example, a low level of labeled secondary antibody bound to the aggregated human IgG indicates a high level of binding of the soluble FcγR to the aggregated human IgG and vice versa.

It is alternatively or additionally likewise possible to analyze, measure or quantify the amount of aggregated human IgG that was removed by washing (before step (c) of the methods of the invention)—said aggregated human IgG is bound to the soluble FcγR of interest (which was comprised in the composition) and is washed out together with it.

The "contacting step" of the methods of the invention involves bringing the surface, the receptor and the aggregated human IgG into physical contact with each other, so that they can bind to each other. This step may involve an incubation step, so that the reagents have time to react.

The term "set amount" simply indicates that the amount of the respective reagents should be fixed, so that the results can be estimated or even quantified. For example, and as can be seen from the examples below, a standard amount of aggregated human IgG was employed with a serial dilution of the soluble receptor, so that the amount at which the soluble receptor inhibits aggregated human IgG binding to the surface can be determined.

The washing step of the method of the invention, involves the removal of unbound aggregated human IgG and unbound soluble human FcγR by "washing" prior to step (c). It should be noted that this step refers to the removal of reagents that are not bound to the surface used in the method. The washing step can be performed with any standard buffer, such as the FACS buffer used in the examples below.

When applied to a serial dilution of the soluble FcγR of the invention, the "detection" of the label allows the determination of the $IC_{50}$ of the soluble FcγR. The "half maximal inhibitory concentration ($IC_{50}$)" is a measure of the effectiveness of a compound in inhibiting biological or biochemical function. This quantitative measure indicates how much of a particular drug or other substance is needed to inhibit a given biological process by half. In other words, it is the half maximal (50%) inhibitory concentration (IC) of a substance (50% IC, or $IC_{50}$). It is commonly used as a measure of antagonist drug potency in pharmacological research. According to the FDA, $IC_{50}$ represents the concentration of a drug that is required for 50% inhibition in vitro. Thus in the present context, the amount of aggregated IgG bound to the mammalian cells compared to the amount of aggregated IgG used in the method allows the determination of the amount of the FcγR needed to inhibit 50% of the aggregated IgG binding to the cell. Likewise, the $IC_{95}$ could be measured, which is the amount necessary to inhibit 95% of the IgG binding to the cells. Any other evaluation technique for the data can be used by the person skilled in the art, for example the four parameter logistic method (4PL) according to the European Pharmacopoeia 5.0; 2005; Chapter 5.3 ("Statistical analysis of results of biological assays and tests").

In a particularly preferred embodiment of the in vitro method of the invention, the soluble human receptor is FcγRIIB (SEQ ID NO.: 3), even more preferably SM101 (SEQ ID NO.: 1), the cells are Raji cells, the aggregated human IgG is isolated from a human IgG preparation e.g. BERIGLOBIN™ and the secondary antibody has a fluorescence label being excitable with a laser beam and emitting light at a set wave length being detectable by means of a FACS apparatus.

The invention also relates to a kit comprising a surface of the invention and/or the aggregated human IgG of the invention. Said kit may further comprise means which are necessary to conduct the methods of the invention (e.g. a label, buffers, reference values, controls, standards etc.).

The invention also relates to aggregated human IgG as disclosed herein.

In the experiments described below, it was found using the in vitro method of the invention that SM101 (soluble human FcγRIIB, SEQ ID NO.: 1) competes with cell-bound FcγRIB on Raji cells for the binding to aggregated IgG, and that increasing concentrations of SM101 added to constant amounts of cells and aggregated BERIGLOBIN™ results in the progressive inhibition of aggregated IgG binding to membrane bound FcγRIIB. This test allows for the determination of possible dosages of SM101 necessary for medical or diagnostic applications. The method can also be used in quality control of SM101 to make sure that different batches have constant binding activity. Likewise, the method can be applied to any other soluble FcγR in order to determine possible dosages and as a quality control to ensure that different batches of soluble FcγR have the same binding activity. Thus the in vitro method of the invention provides a new test for the binding activity of soluble FcγRs based on the finding that aggregated IgG can be used to mimic IgG immune complexes in vitro.

Specifically, in example 1 below, the in-vitro method of the invention, also called "the Cell-based Potency Assay for SM101", allows for a determination of the biological function/activity of SM101. The use of the established human B cell line Raji and polyclonal aggregated human IgGs (BERIGLOBIN™, aggregated fraction) represents an excellent set-up for analyzing the activity of SM101 by means of a cell-based assay. In the examples, SM101 has shown inhibition of binding of aggregated human IgGs to membrane-bound FcγRIIB on Raji cells in several separate FACS-experiments. A serial dilution of SM101 was used to determine the $IC_{50}$ values for SM101. In Example 1 below, the serial dilution with end concentrations of 0.5, 0.25, 0.125, 0.0625, 0.03125, 0.01565, 0.0078, 0.0039, 0.00195 μg/μl was used, though the series 1.3664, 0.80, 0.40, 0.20, 0.10, 0.06, 0.036, 0.0216, 0.01296, 0.00648, 0.003888, 0.001944 μg/μL or any other dilution series that allows for a linear curve in the area of interest though other concentration series could also be used. The measured apparent $K_D$ of $0.98 \times 10^{-6}$ M is comparable to data found in the literature of $1.4 \times 10^{-6}$ M using insect cell derived (glycosylated) soluble FcγRIIB (Sondermann et al., Biochemistry 1999, 38(26):8469-77) or of $1.67 \times 10^{-6}$ M using recombinant sFcγRIIB from E. coli (Maenaka et al., J Biol Chem. 2001, 276(48):44898-904). The calculated $IC_{50}$ of SM101 of 17.7 μg/mL (Example 1) fits with the $IC_{50}$ values as determined in other assays.

In example 1.6 the inventors were able to show that the biological activity of investigational medicinal product of SM101 is comparable to that of the reference standard. Specifically, regarding the claimed method of determining the binding activity, example 1 provides a detailed protocol for soluble human FcγRIIB using Raji cells. The skilled person would be well aware of the adjustments necessary to adapt this method to other receptors and cell types. The exemplary protocol used in Example 1 is repeated below, but the skilled person is well aware of possible variations on this protocol:

1. Determine cell concentration of a Raji cell culture
2. Harvest Raji cells by centrifugation
3. Prepare Fc gamma receptor (e.g. SM101) concentration series in well plate
4. Prepare aggr. BERIGLOBIN™ buffer="aggr. Beri-Mix"
5. Resuspend Raji cells from step 2 in the "aggr. Beri-Mix" from step 4

6. Add Raji cell suspension to each well containing the Fc gamma receptor (e.g. SM101) concentration series
7. Incubate on ice
8. Add "FACS-buffer" to each well, and centrifuge
9. Discard supernatant
10. Add secondary antibody-mix to each well
11. Add "FACS-buffer" and centrifuge
12. Discard supernatant
13. Add "FACS-buffer" and transfer sample to polystyrene tubes and analyse on FACS.

Example 2 provides a specific method for the isolation of aggregated IgG from BERIGLOBIN. Again, the skilled person would be well aware of the possible variations of this method that would lead to a similar result. Specifically, the method for the production of aggregated IgG disclosed here can be summarized by the following steps:
1. Adjust BERIGLOBIN™ 160 mg/mL to 100 mg/mL with PBS-N
2. Separate by preparative SEC (size exclusion chromatography) using a column that can separate aggregated IgG from monomeric or dimeric IgG, e.g. column: Superdex 200 10/300 GL, mobile phase: 5 mM His, 150 mM NaCl pH 6.5, 0.01% (w/v) NaN$_3$, flow 0.5 ml/min at room temperature, injection: 100 μl with 0.4 g/l (see FIG. 12)
3. Determine protein content of aggregated IgG fraction
4. Optional: if content <0.50 mg/mL concentrate by ultrafiltration or if content >1.40 mg/mL dilute with PBS-N (Phosphate buffered saline with 0.02% sodium azide)
5. Adjust to 20% (v/v) glycerol
6. Aliquot at 0.5 mL and snap-freeze in liquid nitrogen.

The aforementioned method for the isolation of aggregated IgG is also applicable to any other human IgG preparation, for example, as is available in the art or described herein.

In example 3, the content and purity of the aggregated IgG isolated according to example 2 was tested. Thus examples 2 and 3 provide the skilled person with specific guidance on the aggregated IgG to be used in the method of the invention. Specifically, using SEC (size exclusion chromatography) at 1 mL/min using PBS-N (phosphate buffered saline with 0.02% sodium azide) as a buffer the aggregated IgG was found to elute after approximately 115 mL when using a Superdex 200, HiLoad 26/60, GE Healthcare, using Äkta Explorer 10 FPLC or any other suitable FPLC. The protein content of the eluate was then measured according to Step 1 of example 3 and, if necessary adjusted to a value between 0.30 and 1.4 mg/mL, preferably between 0.50 and 1.35 mg/ml, even more preferably between. After this, the purity content of the aggregated IgG was measured according to the method of example 2, Step 2 and it was ensured that the relative peak area of aggregated/oligomeric IgG was at least 70%, preferably at least 80%, 90% and most preferably at least 95%.

The robustness of the method of the invention was further studied in prevalidation experiments (Examples 4-10), testing for the influence of the quality of used aggregated IgG, effect of varying amounts of monomeric IgG in the test sample, stability of expression of membrane-bound FcγRIIB on cultivated or freshly thawed Raji cells, effect of blockage of membrane-bound FcγRIIB on Raji via monoclonal antibody and for the stability of background staining of used anti-human secondary antibody on Raji cells. Inter- and Intra-assay stability was assessed by comparing obtained mean values of apparent $K_D$ and $IC_{50}$ of n=25 experiments. Thus it can be concluded, that the in-vitro method of the invention (the cell-based Potency Assay) is a suitable tool to assess the potency of new batches of SM101 compared to reference standard.

The above findings and the specific methods and protocols described in the examples could also be applied to FcγRIIA, FcγRIIIA or FcγIIIB in combination with suitable cells such as human erythroleukemic cell line K562 for FcγRIIA or human NKL cells for FcγRIIIA. Alternately, chinese hamster ovary cells (CHO cells) could be transfected with the FcγR of interest and used in the in-vitro method of the invention. With respect to the methods of preparing aggregated IgG of Example 2 and the controls of Example 3, these methods would apply equally to other human IgG preparation products on the market such as VARITECT™ or VENBIG™, which could be used instead of BERIGLOBIN™.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

As described herein, "preferred embodiment" means "preferred embodiment of the present invention". Likewise, as described herein, "various embodiments" and "another embodiment" means "various embodiments of the present invention" and "another embodiment of the present invention", respectively.

BRIEF DESCRIPTION OF THE FIGURES

The patent or application file contains at least one drawing executed in color. Copies of this patent or patent application publication with color drawing(s) will be provided by the Office upon request and payment of the necessary fee.

The Figures show:

FIG. 13: Table 1: Normalized values calculated for the FACS measurement shown in FIG. 2 that were used for the subsequent fitting of the Langmuir isotherm.

FIG. 14: Table 3: Values obtained from the FACS measurement used for fitting of the Langmuir isotherm (Data from FACS021).

FIG. 15: Table 6: The MFI of Raji cells stained with anti-human IgG(H+L)-PE secondary antibody (1/100 dilution), mean value of samples and standard deviation. Colours indicate experiments that were executed in parallel (intra-assay stability).

FIG. 16: Table 7: The $K_D$, $IC_{50}$ and cell density of Raji cells prior to harvest of 25 FACS-experiments is shown. Experiments 12-15 and 16-17 represent intrasassay stability since $K_D$ and $IC_{50}$ were assessed in separate tests on a single plate. Test #4 and 6 (highlighted in grey) have been excluded from subsequent analysis since the measured data were showing obvious outliers.

FIG. 17: Table 8: Mean value, Standard Deviation and Mean Deviation of $K_D$ and $IC_{50}$ of 25 experiments from Table 8.

FIG. 18: Table 9: Mean $K_D$ and $IC_{50}$ values of tests #1-17 and #18-25.

EXAMPLES

Figure 1:
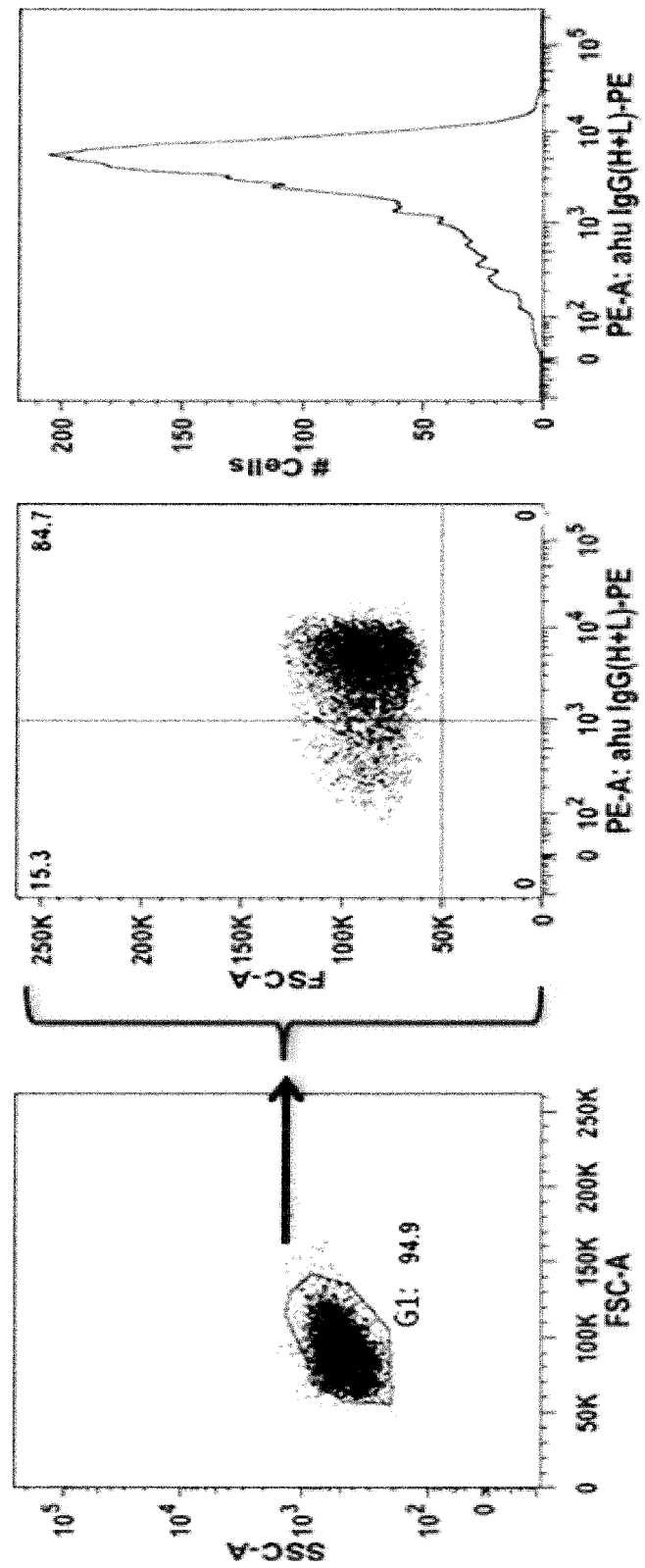
FIG. 1: Gating strategy for FACS analysis showing SSC-A/FSC-A of 1×10$^5$ Raji cells. G1 comprises viable cells (94.9% of total cells). Viable cells are analyzed for binding of secondary antibody (αhu IgG(H+L)-PE) to membrane-bound aggregated human IgG (aggr. BERIGLOBIN™) in absence of SM101. Dot-Plot diagram included for illustration of population distribution only, histogram plot on the far right side depicts Raji cells with bound human aggregated IgG (aggr. BERIGLOBIN™).

The following examples illustrate the invention. These examples should not be construed as to limit the scope of this invention. The examples are included for purposes of illustration and the present invention is limited only by the claims. The following abbreviations are used in the Examples (and in the description):

g earth's gravitational acceleration
C high performance liquid chromatography
MWCO molecular weight cut-off in kDa
PBS-N Phosphate buffered saline with 0.02% sodium azide
rpm rounds per minute
SEC size exclusion chromatography
FSC Forward Scatter
SSC Sideward Scatter
IgG Immunoglobulin G
PE Phycoerythrin
FACS Fluorescence Activated Cell Sorting
DSMZ Deutsche Sammlung von Mikroorganismen und Zellkulturen
ELISA Enzyme Linked Immunosorbent Assay
IMP Investigational medicinal product
AU Absorbance Units Example 1

1.1 Summary of the Experiment

In this example the in vitro method of the invention (also called FACS potency assay) was used to determine the binding activity of SM101 (soluble human FcγRIIB, sFcγRIIB).

Specifically, human cells of the cell-line Raji (DSMZ #ACC319, human Burkitt Lymphoma) expressing FcγRIB were incubated with a constant amount of aggregated ligand (human IgG) and varying amounts of SM101 (i.e. sFcγRIIB SEQ ID NO.: 1). SM101 competes with the cell-bound FcγRIIB-protein, representing the only (IgG-binding) Fcγ receptor expressed on Raji.

Aggregated IgG bound by FcγRIIB expressing cells can be detected by means of fluorescence labelled polyclonal secondary antibody recognizing both heavy and light chain of human IgG followed by FACS analysis of the cells. Increasing concentrations of SM101 added to constant amounts of cells and aggregated IgGs results in a progressive inhibition of IgG binding to membrane-bound FcγRIIB. Parallel control samples with unstained cells as well as cells incubated exclusively with secondary antibody are used to determine both autofluorescence of the used cells and unspecific binding of secondary antibody.

FACS-analysis was carried out by recording $1 \times 10^4$ viable cells on a Becton, Dickinson & Company (BD) FACS-Canto-II machine using BD FACS-Diva software. Data was evaluated using FlowJo Software (Treestar Inc. OR/USA).

1.2 Materials:
Plates: U-shape 96 well (Cellstar, #650180)
Tubes: 15 mL Falcon tubes
    5 mL Polystyrene 12×75 mm (BD, #352054)
Pipettes: sterile, filtered 10 mL, 5 mL (TPP #94010, 94005), graduated Filter tips 1-200 µL, 101-1000 µL (StarLab, #S1120-8810 and S1126-7810)
Microplate adhesive tape (83 mm, 66 m, Permacel, #25082)
SM101 (sFcγRIIB) reference standard:
    8.2 mg/mL, 416 µM stored at −80° C.
FACS-buffer:
    HBSS (Gibco, #14175)+5% FCS (Gibco, #10270-106)+0.01% (w/v) Sodium azide (Merck)
Cell culture medium:
    TM-Medium:
    RPMI (Gibco, #31570)+1% MEM NEA (Gibco, #11140)+1% Sodiumpyruvate (Gibco, #11360)+2 mM GlutaMAX-1 (200 mM Stock solution, Gibco, #35050-061)+10% FCS (Gibco, #10270-106)
IgG (aggregated BERIGLOBIN™):
    IgG 0.96 mg/mL in PBS/0.02% (w/v) sodium azide with 20% (v/v) glycerol, stored at −80° C. Isolated by size-exclusion chromatography on Superdex-200 (16/60) or Superdex 200 (10/300) GL. Starting material: BERIGLOBIN (ZLB Behring GmbH, Ch.-B. 23840311B or Ch.-B. 26840311A; 5 mL ampule) or SUBCUVIA Ch.-B. BVNG1M032A
Secondary antibody:
goat anti-human IgG (H+L) R-phycoerythrin conj. (Fab)$_2$ Fragment (Dianova, Cat. No 109-116-088).

1.3 Protocol:
1. Determine cell concentration of a Raji cell culture with a density of $0.2$-$1.0 \times 10^6$ cells/mL
2. Harvest $1.2 \times 10^6$ Raji cells, centrifuge 5 min at 477×g in a 15 mL Falcon tube
3. From here on, all steps should be performed on ice or at 4° C.
4. Prepare SM101 concentration series in 96 well plate (U-bottomed) starting with 1.0 µg/µL SM101 and ending with 0.0039 µg/µL (Diluent: "FACS-buffer") as well as control samples (0 µg/µL SM101 to be used for secondary antibody only) by adding 50 µL™-Medium to corresponding control wells
5. Prepare 500 µL of a 50 µg/mL aggregated BERIGLOBIN™ in FACS-buffer (e.g. by adding 26.04 µL of a 0.96 µg/µL stock to 473.96 µL FACS-buffer)="aggr. Beri-Mix"
6. Resuspend $1.2 \times 10^6$ Raji cells from step 2 in the 500 µL "aggr. Beri-Mix" from step and mix thoroughly (vortex, 30 s, medium speed)
7. Add 50 µL of Raji cell suspension to each well containing the 50 µL SM101 concentration series and control wells (final volume=100 µL)
8. Incubate for 30 min on ice in dark
9. Add 150 µL "FACS-buffer" to each well, seal wells using adhesive tape and centrifuge for 5 min at 513×g
10. Prepare 1 mL of 1/100 secondary antibody-mix in "FACS-buffer"
11. Discard supernatant and vortex plate briefly with seal on wells to avoid cross-contamination
12. Add 50 µL secondary antibody-mix to each well, except unstained control
13. Incubate for 30 min on ice in dark
14. Add 150 µL "FACS-buffer" and centrifuge for 10 min at 513×g
15. Discard supernatant and vortex plate briefly with seal on plate
16. Add 150 µL "FACS-buffer" and transfer sample to 5 mL polystyrene tubes and analyze on BD FACS-Canto II (using BD Diva software v. 6.0).

1.4 Concentration Series for SM101 (End Concentrations):
0.5, 0.25, 0.125, 0.0625, 0.03125, 0.01565, 0.0078, 0.0039, 0.00195 µg/µL; Final volume ($V_{END}$)=100 µL 1.5 FACS Data Analysis FACS-Data was recorded on a BD FACS-Canto II, data saved in the fcs-file format. For subsequent analysis Flow-Jo software (v. 8.8.4) was used. FIG. 1 depicts a typical gating strategy.

Figure 2:
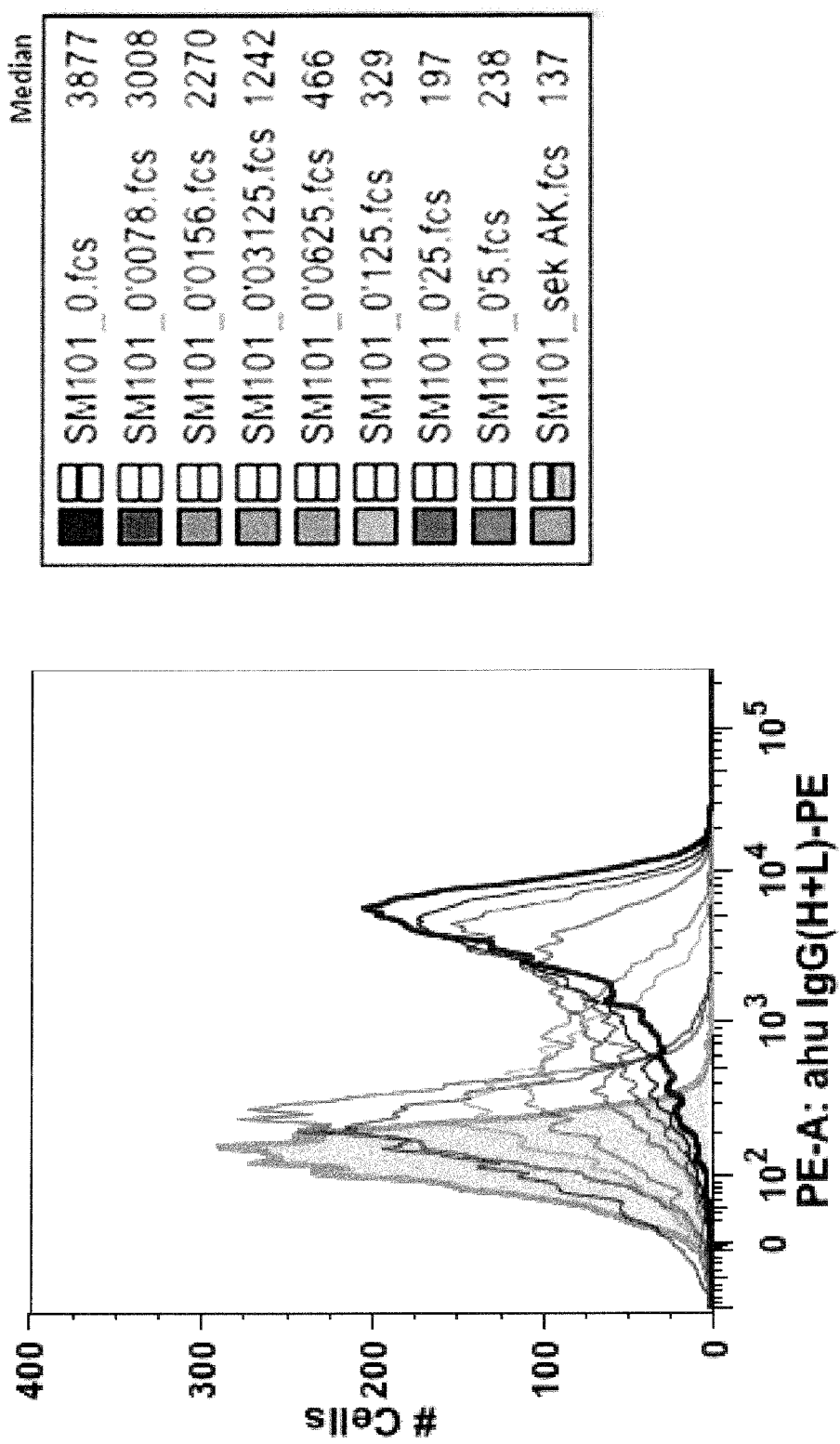
FIG. 2: Overlay of histograms of samples incubated with varying SM101 (soluble human FcγRIIB) concentrations (lowest concentration 0 μg/μL, concentration range of samples 0.0078-0.5 μg/μl). A shift of the corresponding histograms in overlay in direction of negative control (staining with secondary antibody alone (=sek AK, shaded red) indicates inhibition of binding of human aggregated IgGs (aggr. BERIGLOBIN™) to cells. Median of PE-A Fluorescence of samples is shown on right side.
Figure 3:
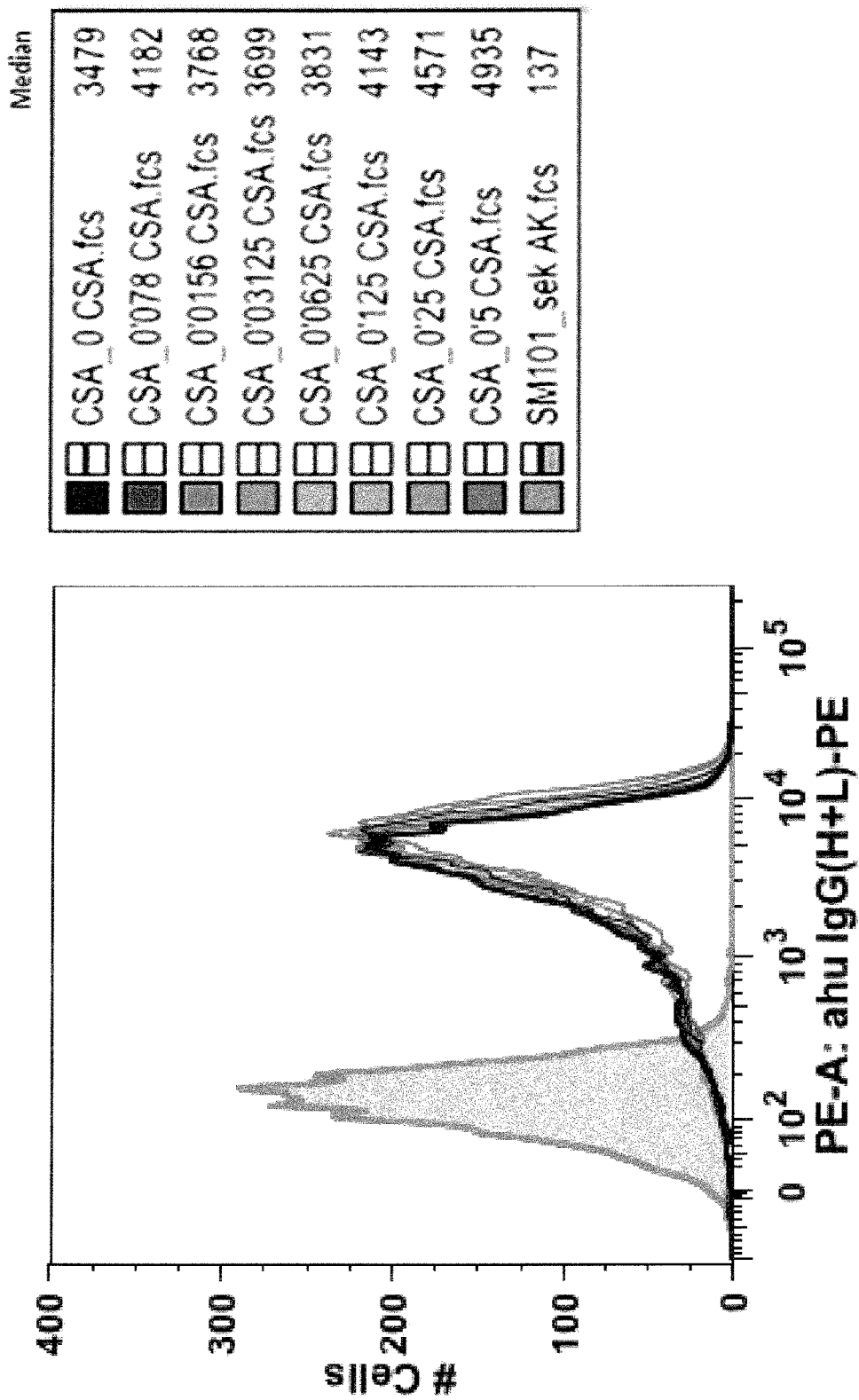
FIG. 3: Overlay of histograms of control experiment using chicken serum albumin (CSA) in varying concentrations in place of SM101 (lowest concentration 0 μg/μL, concentration range of samples 0.0078-0.5 μg/μl). Negative control (SM101_sekAK.fcs; staining of cells with secondary antibody only shaded red).

Viable cells were gated and assessed for their phycoerythrin-fluorescence. Histograms of samples from a SM101 concentration series were grouped in a histogram overlay using FlowJo software. Median Fluorescence Values were calculated by the software for each sample (FIG. 2). FIG. 2 shows a strong concentration dependent inhibition of binding of aggregated IgGs to membrane-bound FcγRIIB on Raji cells. In a parallel experiment SM101 was replaced by identical amounts of chicken serum albumin using the same above mentioned concentration series to confirm specific inhibition by SM101 (FIG. 3). The in vitro method of the invention provides a qualitative cell-based means to assess the binding activity of SM101 as demonstrated by the showcase experiment depicted in FIG. 2.

1.6 Calculation of Activity

Figure 4:
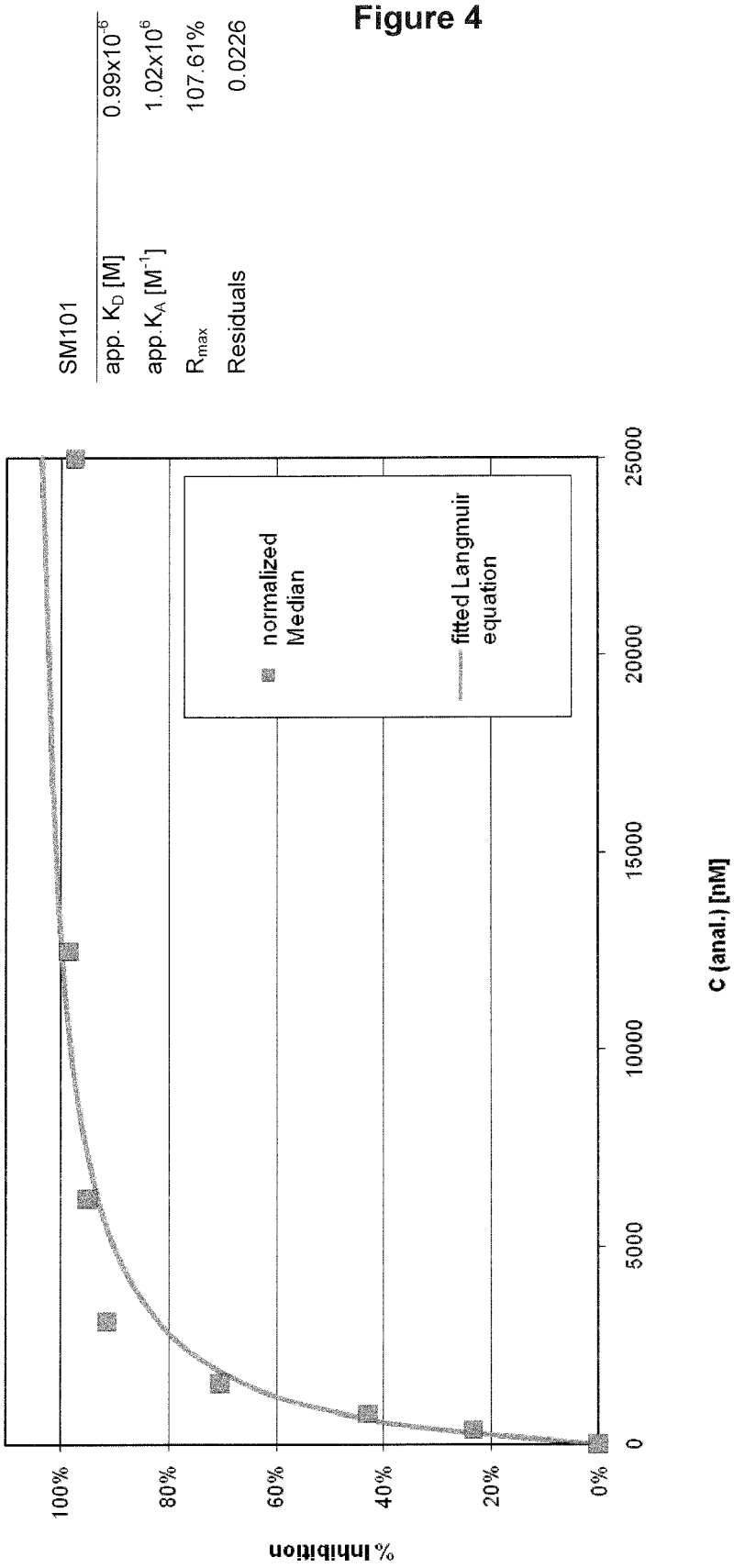
FIG. 4: Normalized measured Median values from Table 1 of Example 1 were fitted to the Langmuir equation.

To calculate the activity of SM101 in this cellular assay the Median Fluorescence Intensity signals were normalized using the following formula (normalized data shown in Table 1 in FIG. 13):

A subsequent fitting of the data to the Langmuir-binding-isotherm formula $$\% \text{ inhibition} = (c \cdot \text{max. inhibition})/(K_D + c)$$

using the Solver-add-in function in Excel was performed for the determination of the apparent $K_D$ and maximum inhibition and resulted in an inhibition-curve as shown in FIG. 4. The apparent $K_D$ might differ from the real $K_D$ since the unknown cell surface concentration of FcγRIIB on Raji cells as well as the concentration of free SM101 cannot be taken into account. For % inhibition the % normalized signal are used, c=concentration of soluble FcR (molar concentration or mass concentration). Formula is fitted for max.inhibition and KD using Solver-add-in function in Excel or any other computer program allowing for this type of calculation.

Using this fitting strategy the FACS-data revealed an apparent $K_D$ of $0.99 \times 10^{-6}$M with a sum of square residuals of 0.0226 (Table 2).

TABLE 2

Parameters obtained for fitting of data from FACS007 to
the Langmuir equation.

SM101

| | |
|---|---|
| app. $K_D$ [M] | $0.99 \times 10^{-6}$ |
| app. $K_A$ [M$^{-1}$] | $1.02 \times 10^6$ |
| $R_{max}$ | 107.61% |
| Residuals | 0.0226 |

The analysis-software MICROCAL™ Origin (Version: 6.0) was used to calculate the $IC_{50}$ of SM101 from the data of the FACS. % inhibition was plotted versus concentration of competitive SM101. The data was fitted to the Sigmoid Logistic Function:

$$y = A2 + \frac{A1 - A2}{1 + \left(\frac{x}{x_0}\right)^p}$$

A2: 100% inhibition (maximal inhibition
A1: 0% inhibition (minimal inhibition)
X0: $IC_{50}$
p: slope Parameter A1 was set to 0 and parameter A2 to 100 for the calculation of $IC_{50}$.

Figure 5:
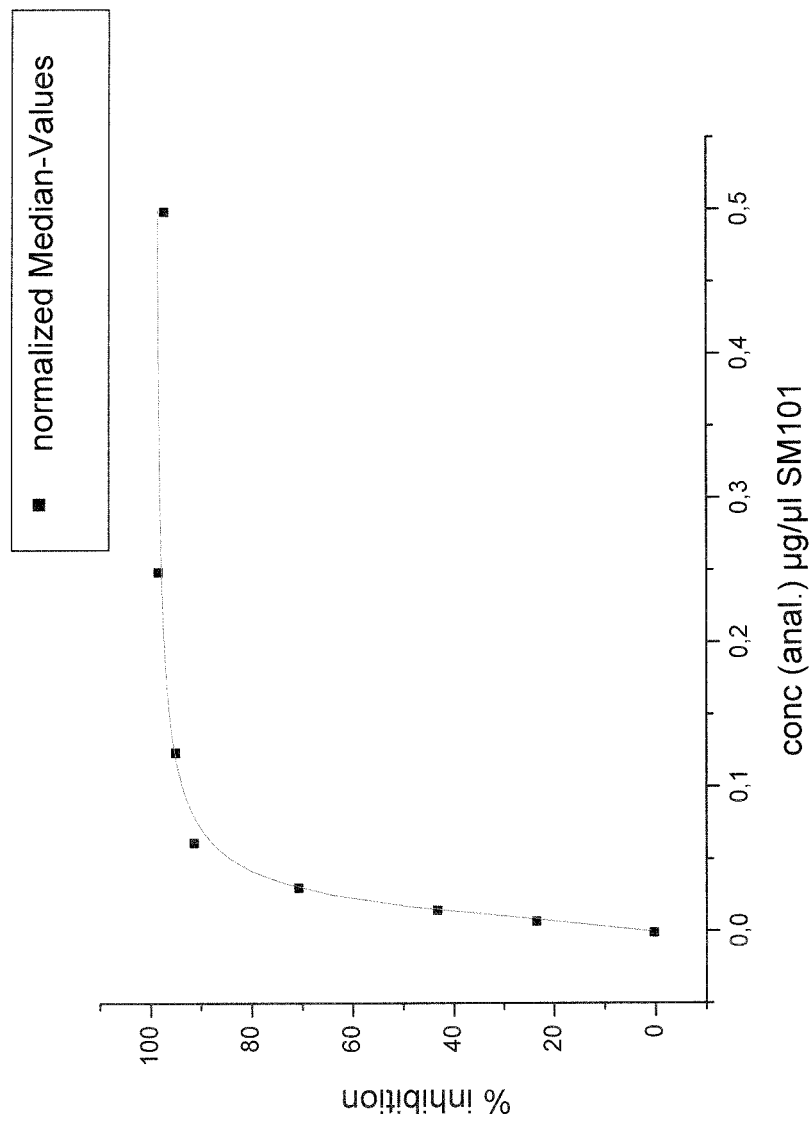
FIG. 5: Data fitted to sigmoid logistic function showing % inhibition versus mass concentration of SM101 (μg/μL) using data from FACS experiment 7 (FACS007)

Using the data from table 1 (FACS007) an $IC_{50}$ of 17.7 μg/mL with a slope 1.63 of was evaluated (FIG. 5).

1.7 Comparison of Reference Standard and SM101

In a subsequent experiment the biological activity of the investigational medicinal product SM101 (sFcγRIIB) was investigated and compared to the drug substance reference standard (FACS21). The FACS-based Potency Assay was conducted as described in item 1.4 above for IMP and reference standard in parallel on a single 96-well plate.

Figure 6:
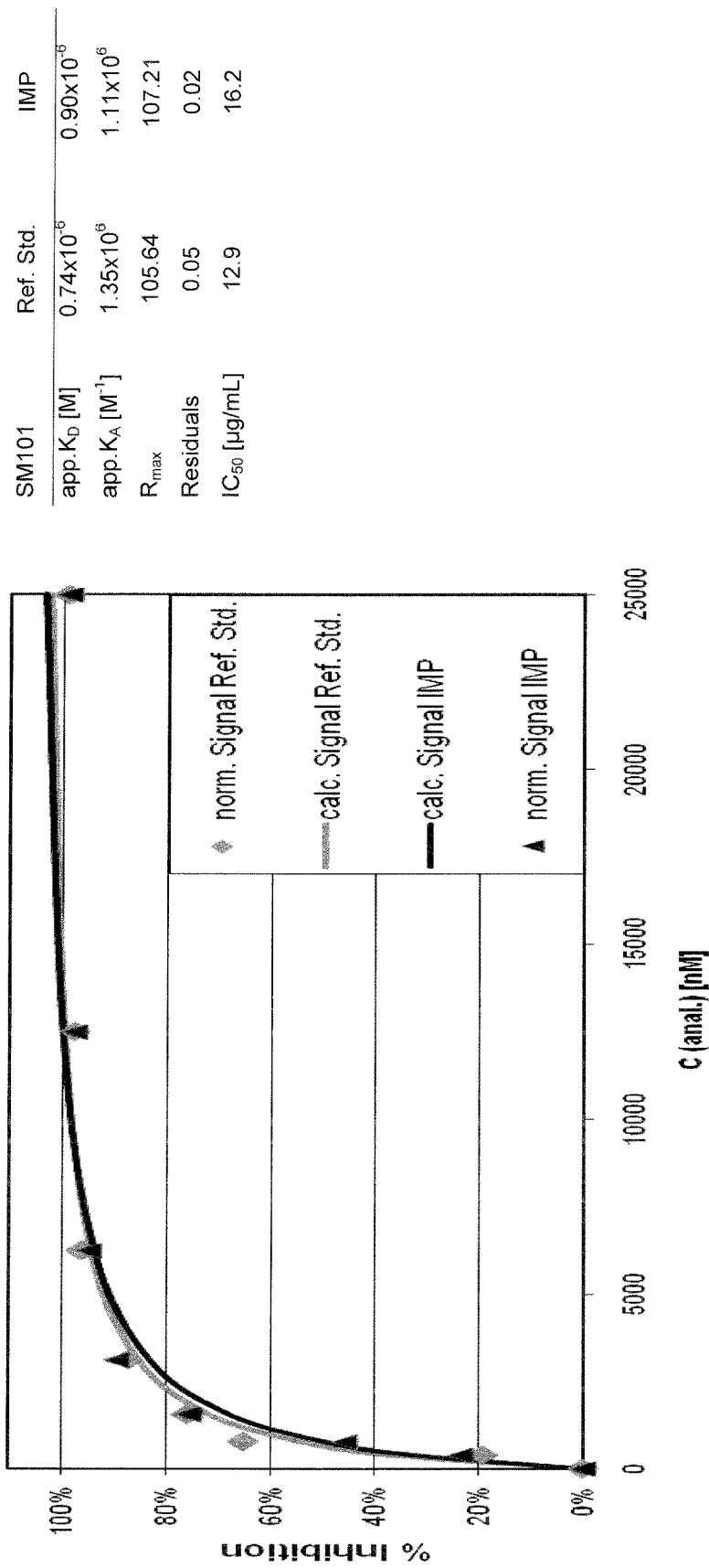
FIG. 6: Langmuir-diagram of data fitted to normalized measured Median values of SM101 reference standard and SM101 IMP as calculated in Table 3 (Data from FACS021).

FACS-data was recorded and analyzed as described (item 1.5 above) and fitting of data was performed using Langmuir-binding-isotherm formula outlined above (Table 3 in FIG. 14 and FIG. 6).

The FACS data revealed an apparent $K_D$ of $0.739 \times 10^{-6}$M for SM101 reference standard and an apparent $K_D$ of $0.904 \times 10^{-6}$M for SM101 IMP (Table 4).

TABLE 4

Parameters obtained for Langmuir- and Sigmoid logistic
function-fitting of data from Table 3, FIG. 6 (FACS021).

| SM101 | Ref. Std. | IMP |
|---|---|---|
| app. $K_D$ [M] | $0.74 \times 10^{-6}$ | $0.90 \times 10^{-6}$ |
| app. $K_A$ [M$^{-1}$] | $1.35 \times 10^6$ | $1.11 \times 10^6$ |
| $R_{max}$ | 105.64 | 107.21 |
| Residuals | 0.05 | 0.02 |
| $IC_{50}$ [μg/mL] | 12.9 | 16.2 |

The analysis-software MICROCAL™ Origin (Version: 6.0) was used to calculate the $IC_{50}$ of SM101 reference standard and IMP from the data of the FACS-analysis using the sigmoid logistic function described above. SM101 reference standard showed an $IC_{50}$ of 12.9 μg/mL and IMP of SM101 of 16.2 μg/mL (Table 4).

Given that an interassay deviation of +/−20% is acceptable in a cellular assay it can thus be concluded that the biological activity, as determined in the FACS-based potency assay, of IMP is comparable to drug substance reference standard of SM101.

Example 2

In this example a method for the preparation of aggregated IgG from a commercial IVIG, BERIGLOBIN™, is described. Aggregated IgG is a raw material for the in vitro method for determining the binding activity of soluble human Fc gamma receptors of the present invention. In this experiment, the following reagents were used:

| Item | Supplier | Quality |
|---|---|---|
| BERIGLOBIN™ 160 mg/mL CSL Behring 5 mL pre-filled syringe | Local Pharmacy | Approval no. 176a/92 |
| NaCl | Roth, or equivalent | p.a. |
| KCl | Merck, or equivalent | p.a. |
| Na$_2$HPO$_4$•2H$_2$O | Sigma, or equivalent | p.a. |
| KH$_2$PO$_4$ | Merck, or equivalent | p.a. |
| NaN$_3$ | Merck, or equivalent | purified |
| Glycerol 98%, anhydrous | Roth, or equivalent | Ph. Eur. |

Figure 7:
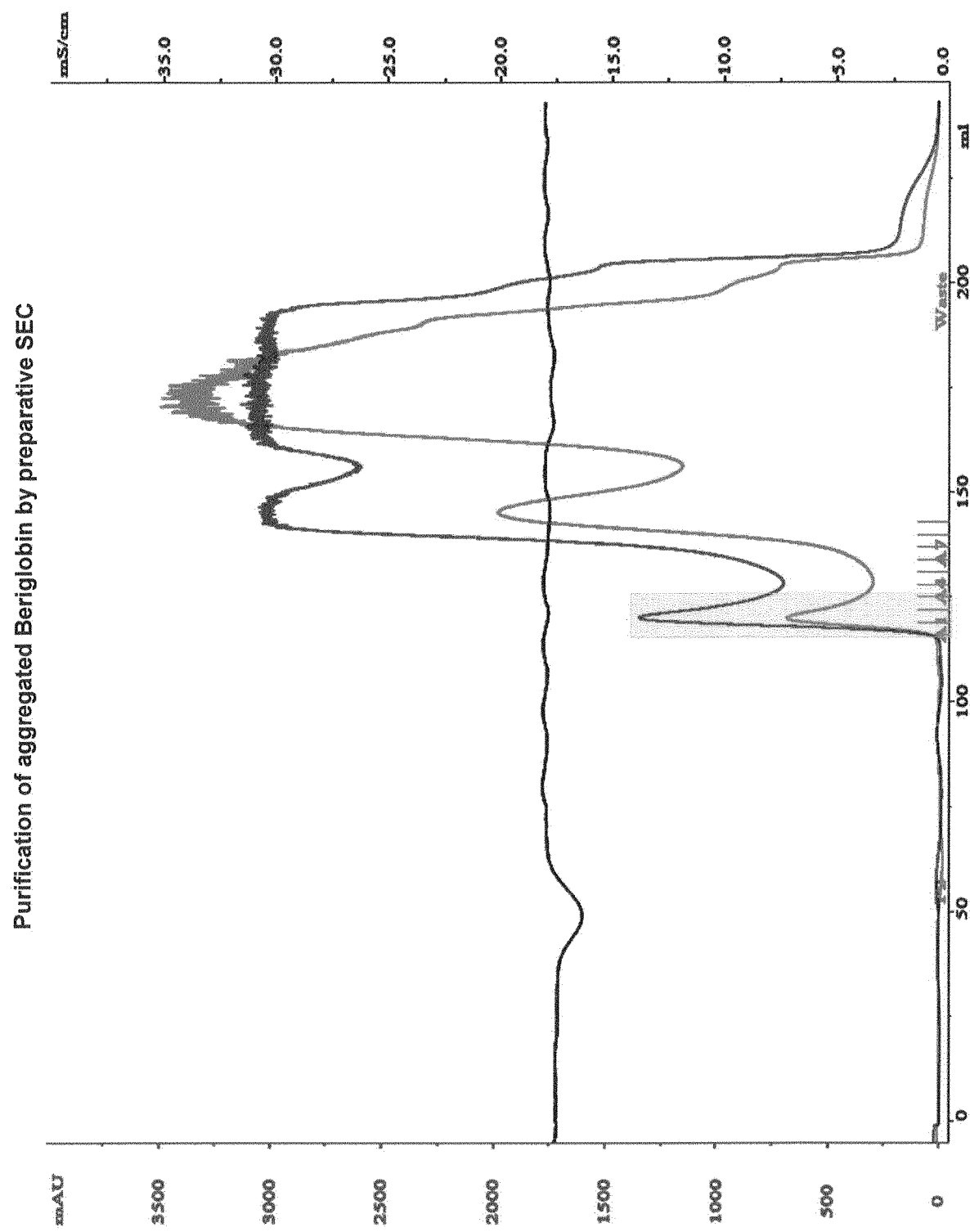
FIG. 7 Purification of aggregated IgG by preparative SEC. The optical density of the eluate at 280 (upper trace), 260 nm (lower trace) and the conductivity (line trace) are shown. The pooled aggregated human IgG fractions are shaded in grey.

The method for the production of aggregated IgG can be summarized by the following steps: 1. Adjust BERIGLOBIN™ 160 mg/mL to 100 mg/mL with PBS-N
2. Separate by preparative SEC
3. Determine protein content
4. Optional: if content <0.50 mg/mL concentrate by ultrafiltration or if content >1.40 mg/mL dilute with PBS-N (Phosphate buffered saline with 0.02% sodium azide)
5. Adjust to 20% (v/v) glycerol
6. Aliquot at 0.5 mL and snap-freeze in liquid nitrogen Specifically, 5 mL BERIGLOBIN™ 160 mg/mL are carefully mixed with 3 mL PBS-N until a homogeneous solution is obtained. 3.0 mL of the dilution is injected at a flow rate of 1 mL/min (Äkta Explorer 10, GE Healthcare) onto a Superdex 200 HiLoad 26/60 column (GE Healthcare) previously equilibrated in PBS-N. The proteins are separated at 1 mL/min using PBS-N as buffer. Aggregated IgG elutes after approx. 115 mL and is collected in 3 mL fractions after the optical density of the eluate at 280 nm exceeds 50 mAU. The first three fractions are pooled and stored for a maximum of 3 days at 2-8° C. until they are mixed with the pool from additional SEC runs. If the protein content of the aggregated IgG pool from all SEC runs is below 0.50 mg/mL the pool has to be concentrated by ultrafiltration to 1.00-1.40 mg/mL (Amicon Ultra, Ultracel 100 kDa MWCO, Millipore). If the protein content of the aggregated IgG pool is above 1.40 mg/mL the pool is diluted with PBS-N to 1.40 mg/mL. Finally the cryo-protectant glycerol is added dropwise under constant stirring (500 rpm) to a final concentration of 20% (v/v). The content of the adjusted aggregated BERIGLOBIN™ pool is determined for release and the pool is aliquoted at 0.5 mL in 1.5 mL reaction tubes (Safe seal tubes, Sarstedt). The aliquots are snap-frozen in liquid nitrogen and stored at −60° C. to −80° C. The results of the purification are shown in FIG. 7, where the shaded area represents the pooled aggregated IgG fractions.

Example 3

In this example methods for testing the quality of the aggregated IgG prepared according to the method of Example 2 are described. In a first step, the content of the aggregated BERIGLOBIN™ fractions is measured. In a second step, the purity of the aggregated BERIGLOBIN™ is tested by analytical SEC. The second step is performed with frozen aliquots of the aggregated BERIGLOBIN™. The frozen aliquots have to be thawed at room temperature (25±2° C.) under gentle shaking (500 rpm (rounds per minute), Thermomixer R, Eppendorf) prior to their use.

To minimize testing effort in case of an incongruous batch, quality testing is performed stepwise. The following tests are performed at each step of testing:

| Step | Item | Method/Plan # | Targeted value |
|---|---|---|---|
| 1 | Content | UV/VIS spectroscopy | 0.30 mg/mL ≤ $C_{agg.\ BERIGLOBIN™}$ ≤ 1.35 mg/mL |
| 2 | Purity | analytical SEC | relative peak area aggregated/oligomeric BERIGLOBIN™ >70% |

Step 1: Content Measurement by UV/VIS Spectroscopy

The content of the aggregated BERIGLOBIN™ fractions produced according to the method of Example 1 can then be measured by UV/VIS spectroscopy. If necessary, the protein solution is diluted with the respective buffer to give an optical density at 280 nm between 0.2 and 0.8. 400 μL of the solution are transferred to a UV-microcuvette (UV-cuvette micro, Brand). The absorbance at 280 nm and 320 nM is recorded (Cary 100 Bio, Varian) against PBS-N as blank and the concentration in mg/mL is calculated according to the following equation:

$$c_{agg.\ BERIGLOBIN™}[mg/mL]=(OD_{280}-OD_{320})/1.40$$

The assay is carried out in triplicate and the results are averaged.

Step 2: Purity by Analytical SEC

The amount of aggregated/oligomeric BERIGLOBIN™ relative to dimeric and monomeric forms is determined by analytical SEC. A series 1200 HPLC system (Agilent) equipped with a Superdex 200 10/300GL column (GE Healthcare) previously equilibrated in PBS-N is used. 150 μL of a freshly thawed aliquot of aggregated BERIGLOBIN™ are centrifuged (20'000·g, 5 min) and 50 μL of the supernatant are injected at a flow rate of 0.5 mL/min. The proteins are separated at a flow rate of 0.5 mL/min using PBS-N as buffer and the absorbance of the eluate at 280 nm is monitored.

Figure 8:
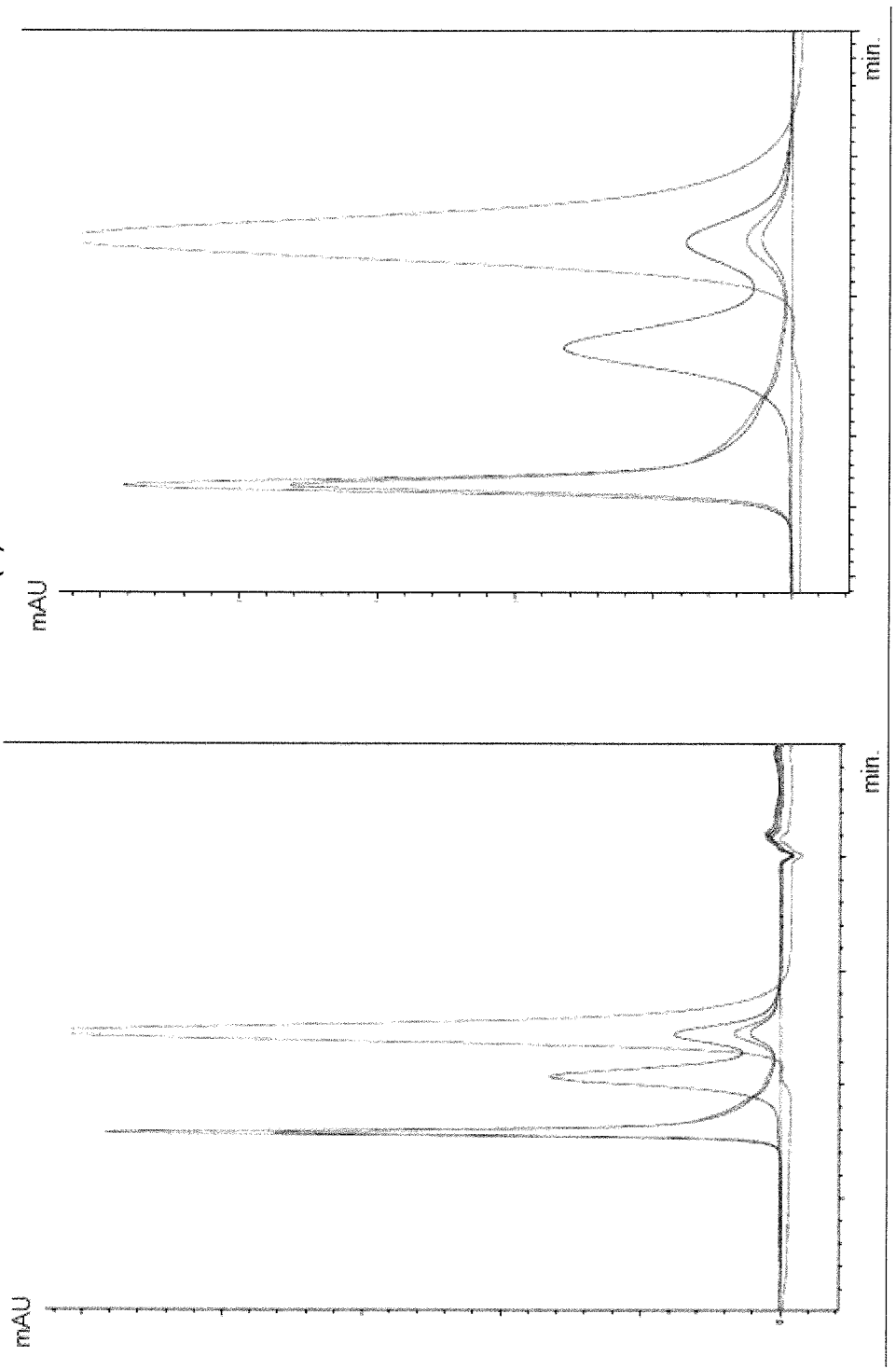
FIG. 8: Analytical SEC of various aggregated human IgG fractions. Chromatograms after blank buffer injection (trace bottom, line), injection of 50 μg monomeric IgG from BERIGLOBIN™ (trace with highest peak) corresponding to the peak at approx. 180 mL in the preparative SEC chromatogram c.f., injection of 50 μg dimeric IgG from BERIGLOBIN™ (trace with lowest peak) corresponding to the peak at approx. 145 mL in the preparative SEC chromatogram c.f., injection of 24 μg aggregated/oligomeric IgG from batch 27/10/10 (lower overlapping first peak) and injection of 24 μg aggregated/oligomeric IgG from batch 15/07/11 (higher overlapping first peak) are shown. The full chromatogram (a) and a zoomed section (b) are presented.
Figure 9A:
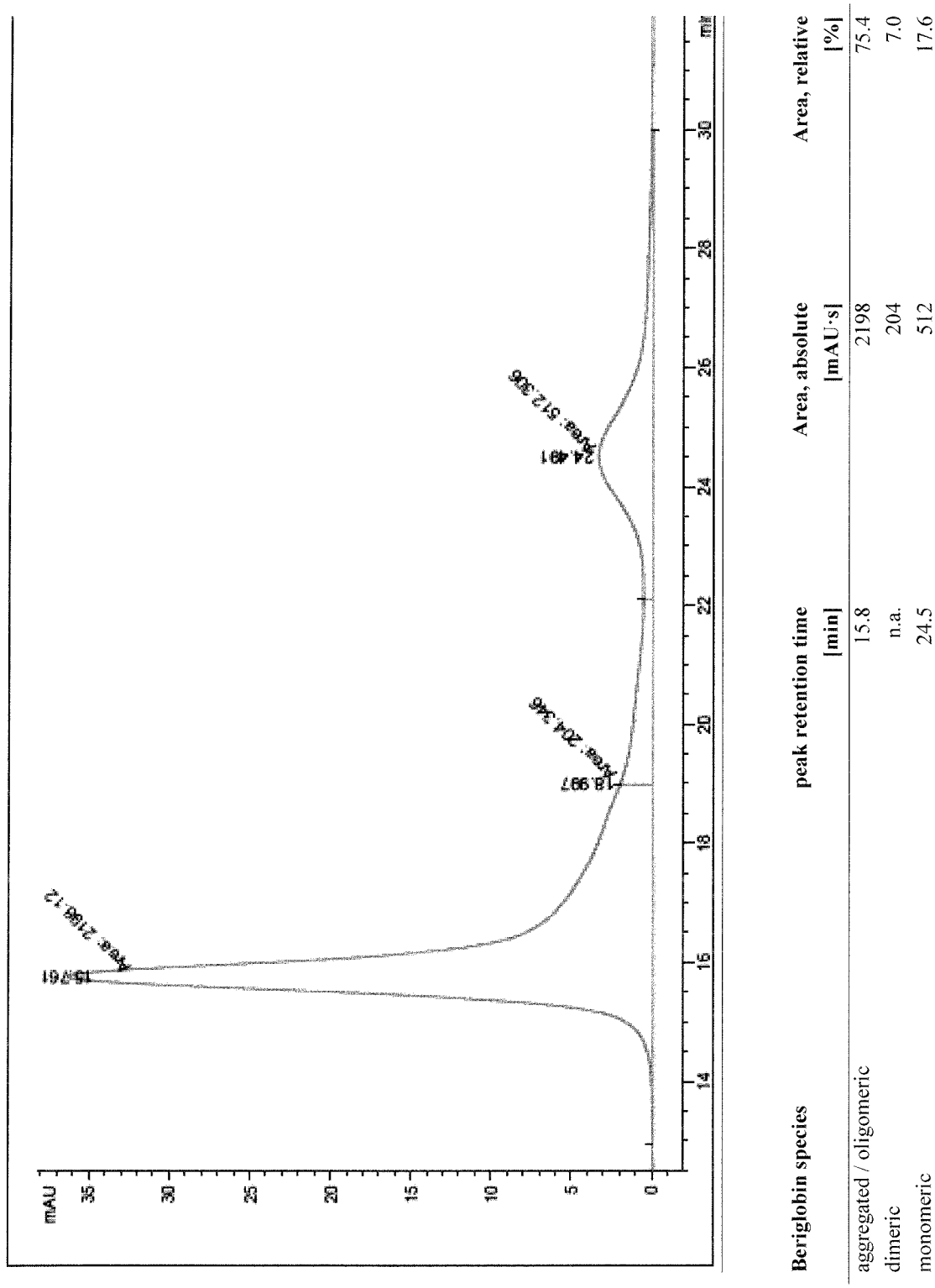
FIGS. 9a/b: Exemplary integration of analytical SEC chromatograms from aggregated human IgG batch 27/10/10 (a) and batch 15/07/11 (b).
Figure 9B:
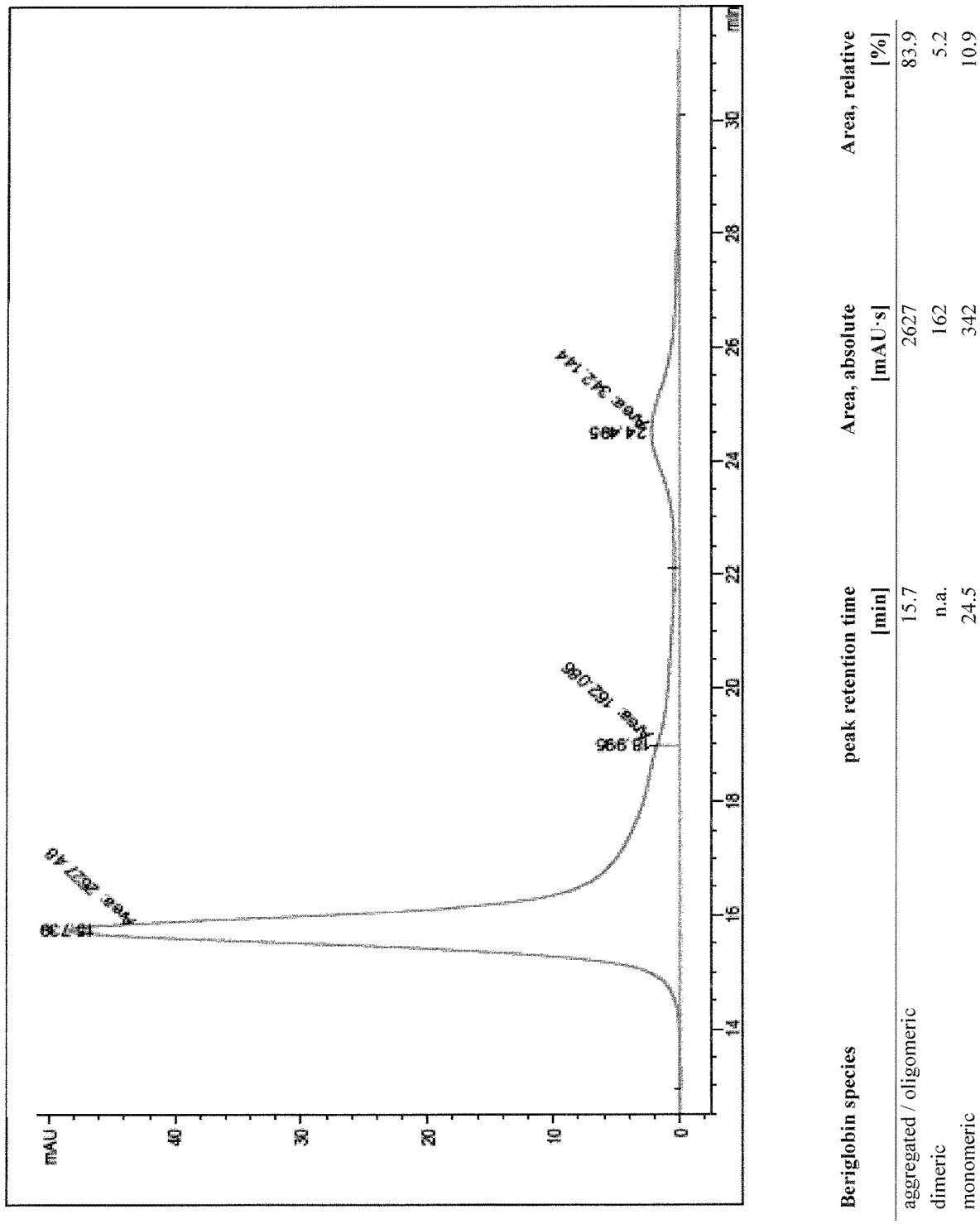

The total run time is limited to 50 min. Each aggregated BERIGLOBIN™ injection is preceded by an injection of 50 μL PBS-N, 20% glycerol. The chromatograms are manually integrated and the purity is reported as the relative area of the aggregated/oligomeric BERIGLOBIN™ peak compared to all peaks from 13.0 min to 30.0 min. Analytical SEC of various BERIGLOBIN™ fractions is shown in FIG. 8. FIGS. 9a and 9b show the exemplary integration of analytical SEC chromatograms from two aggregated BERIGLOBIN™ batches.

Example 4

In this example, experiments were conducted to determine a putative influence of the quantity and quality of aggregated BERIGLOBIN™ on the binding to Raji cells. The experiments were conducted using varying amounts of aggregated BERIGLOBIN™ and different batches of BERIGLOBIN™.

The tested concentrations of aggr. BERIGLOBIN™ comprised 20, 10, 5, 3, and 2.5 μg/1×10⁵ cells. In subsequent experiments, the concentration of secondary antibody (αhu IgG(H+L)-PE was varied concomitant, to determine whether secondary antibody was available in excess compared to aggr. BERIGLOBIN™ (FIG. 10).

Figure 10:
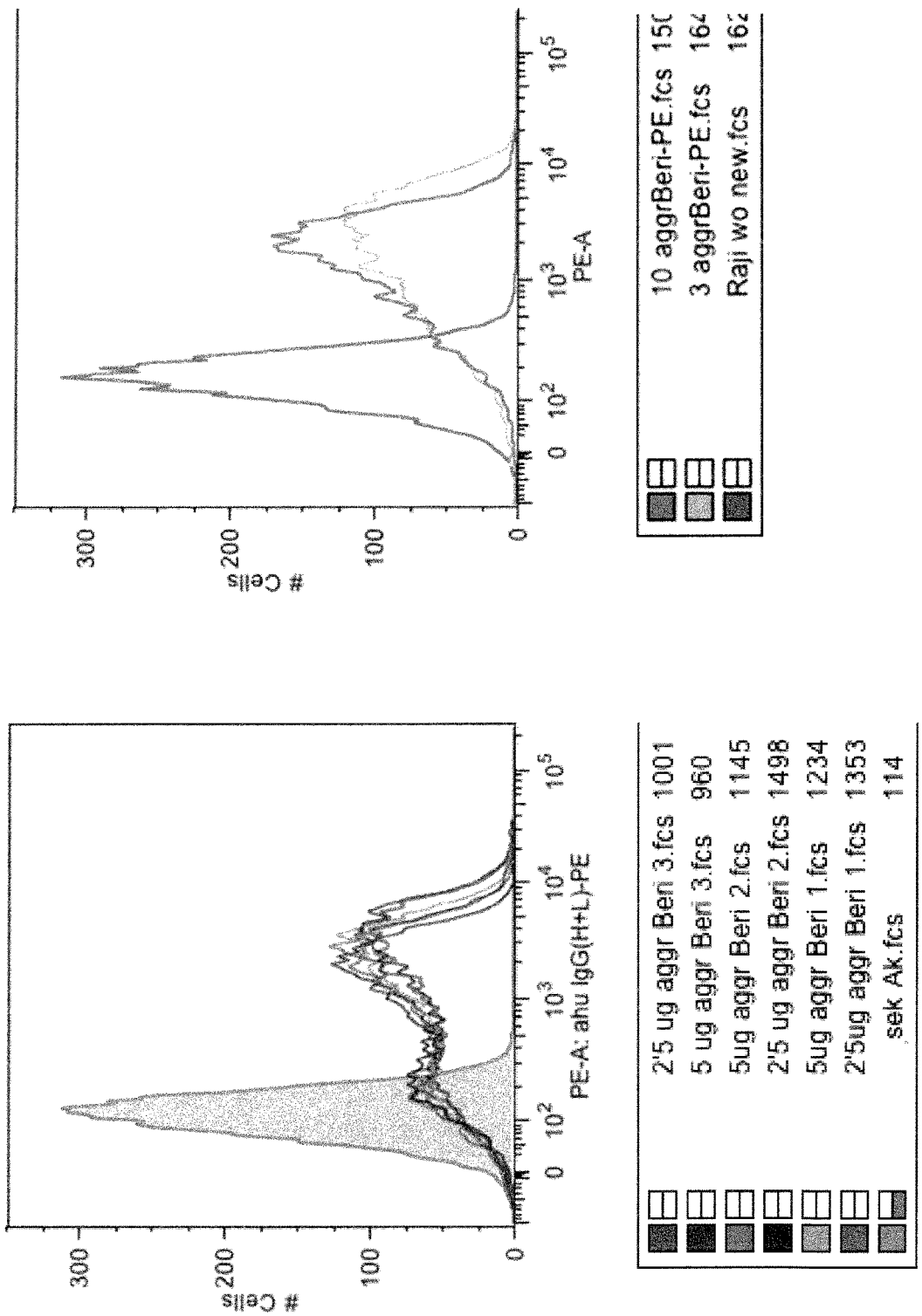
FIG. 10: FACS-Analyses of varying amounts and different batches (Beri 1, Beri 2 or Beri 3) of aggregated human IgG bound to viable Raji cells

As can be seen from FIG. 10, the binding to Raji cells is not limited by the amount of aggregated BERIGLOBIN™ even at the lowest concentration. An amount of 2.5 μg per 1×10⁵ cells ($V_{end}$=100 μL) is sufficient for a quantitative binding to the available receptors on the cells.

Table 5 shows the Median of MFI of different batches of aggr. BERIGLOBIN™ (#1, 2, 3), calculated Mean and SD

| Batch # aggr. Beriglobin | Median MFI 2.5 μg/μL | Median MFI 5.0 μg/μL |
|---|---|---|
| 1 | 1353 | 1234 |
| 2 | 1498 | 1145 |
| 3 | 1001 | 960 |
| Mean | 1284 | 1113 |
| SD | 256 | 140 |

Example 5

Figure 11A:
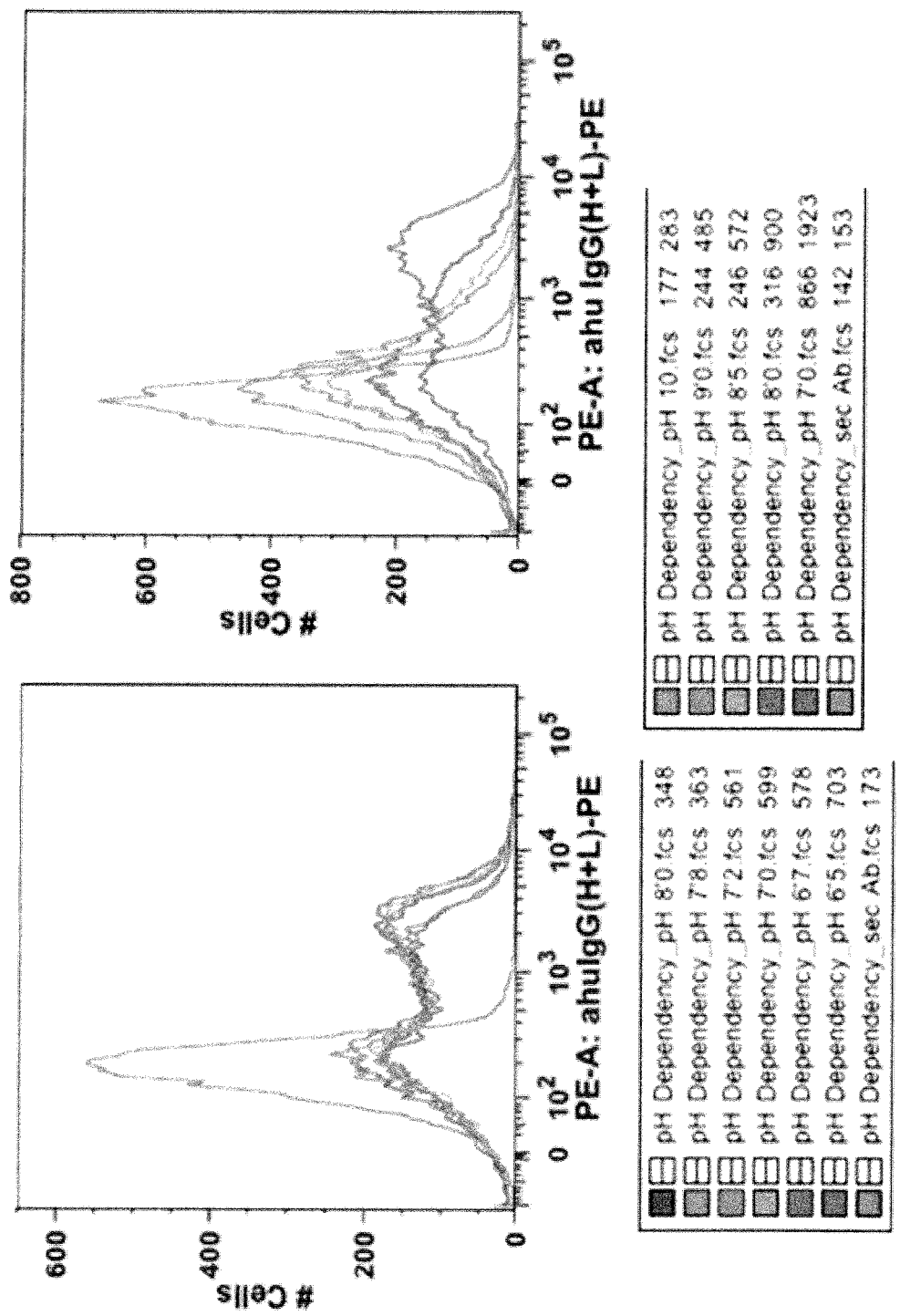
FIG. 11: (a) pH dependency of binding of aggregated IgG to Raji cells (Median MFI)
(b) Median MFI of pH dependency. Graph showing Median MFI of sample—Median MFI of secondary Antibody (control)
Figure 11B:
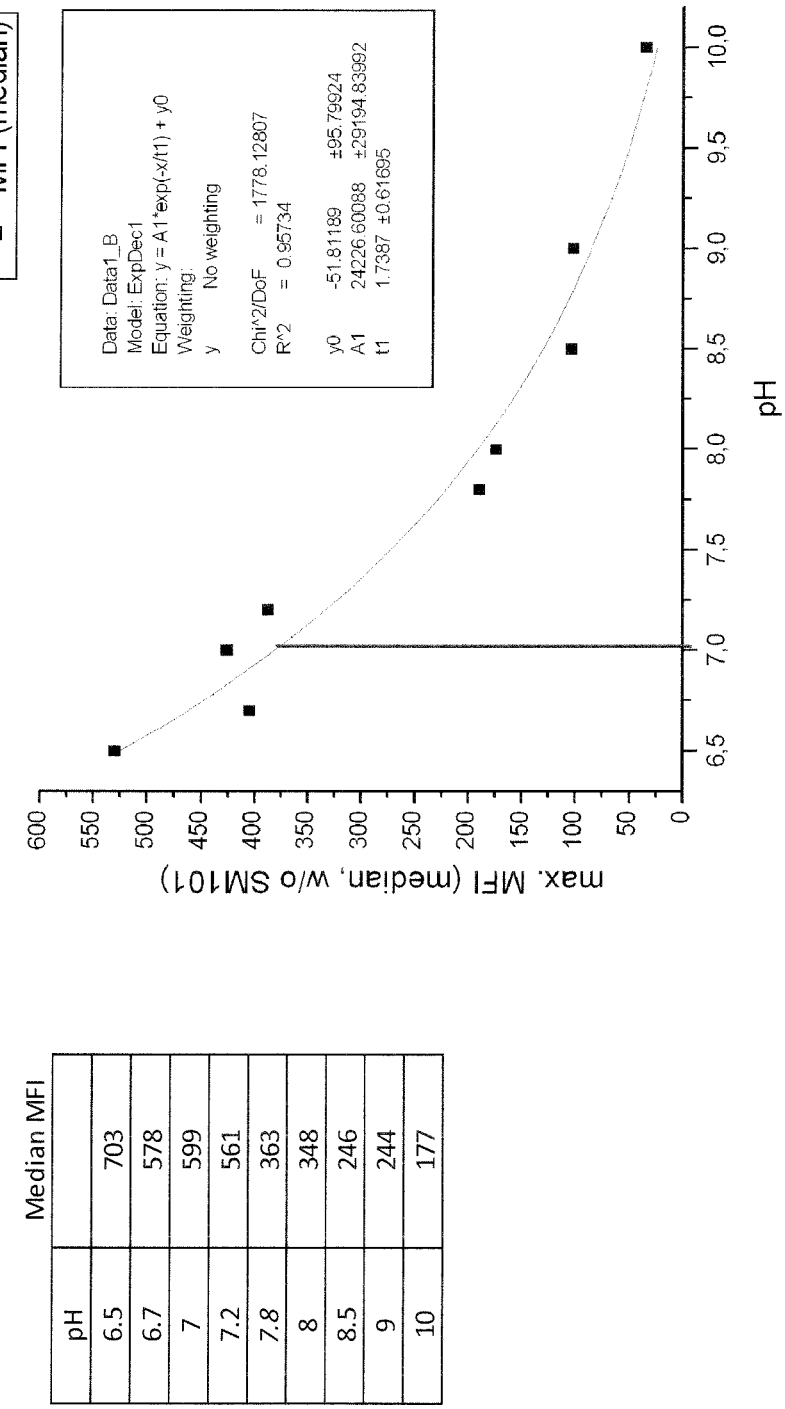
Figure 12:
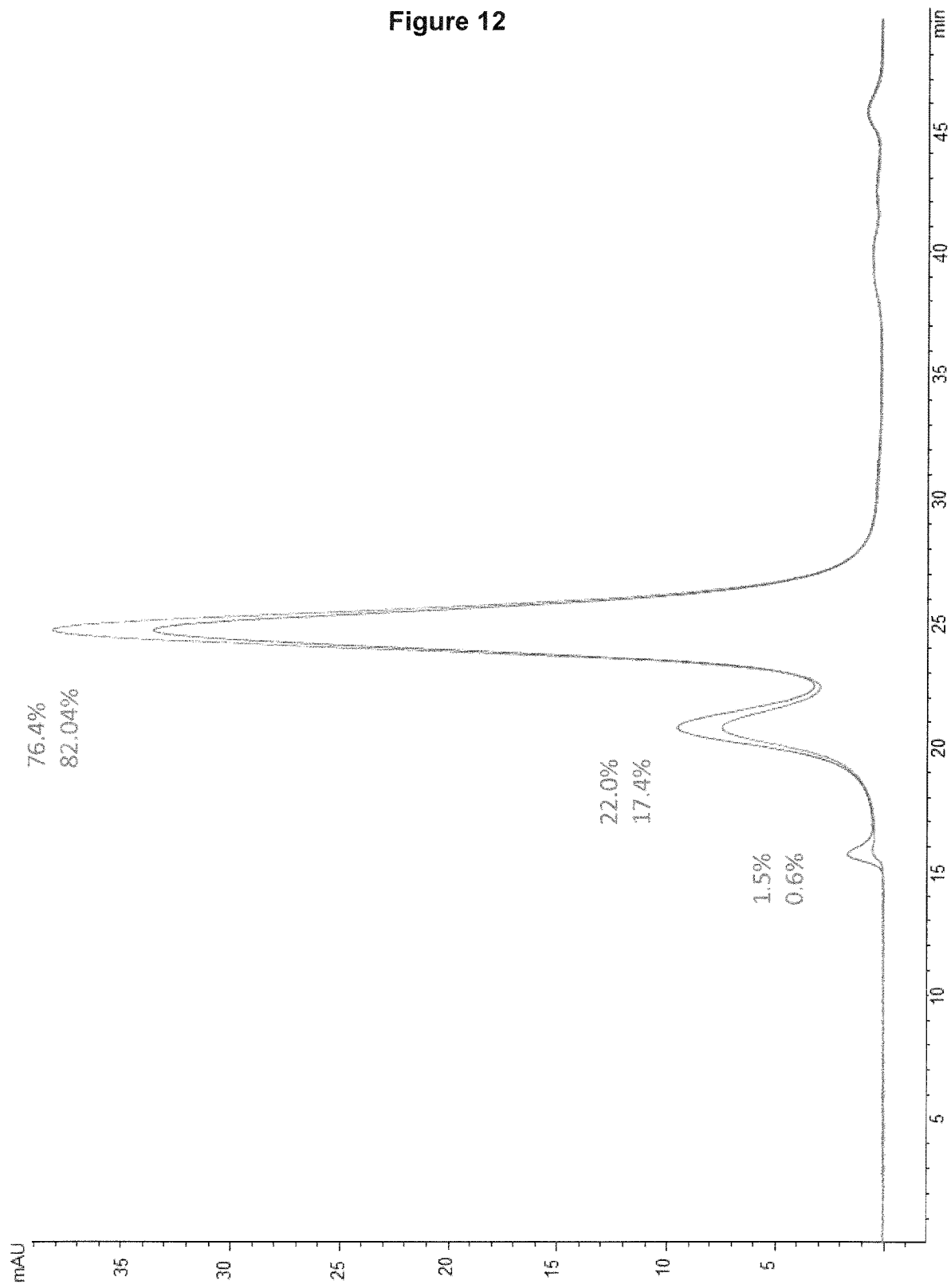
FIG. 12: Isolation of aggregated IgG from two available pooled IgG preparations (BERIGLOBIN™ batch No. 26840311A and SUBCUVIA™ batch No. BVNG1M032A), column: Superdex 200 10/300 GK; mobile phase: 5 mM His, 150 mM NaCl pH 6.5, 0.01% (w/v) NaN$_3$; flow: 0.5 ml/min at room temperature; injection: 100 μl with 0.4 g/l.

In this experiment, the pH-Dependency of the binding of aggregated BERIGLOBIN™ to Raji cells was investigated. The medium used for the method of the invention as described in example 1 (FACS-Potency-assay) contains RPMI, MEM, Na-Pyruvat, 10% FSC and a L-Glutamin source (Glutamax-I, Gibco). L-Glutamin over time degrades to PCA and $NH_3$ leading to a alkaline pH. Even though Glutamax-I has a reduced degradation tendency, the pH of the culture medium gets more alkaline over time. To test for the pH dependency of the binding of aggregated BERIGLOBIN™ to Raji cells, 0.1E6 Raji cells were incubated with 2.5 μg aggr. BERIGLOBIN™ at various pH conditions (pH 6.5, 6.7, 7.0, 7.2, 7.8, 8.0, 8.5, 9.0, 10.0) and the binding aggr. BERIGLOBIN™ to cells was assessed in a FACS assay using a 1/200 αhu IgG(H+L)-PE secondary antibody. As can be seen from FIGS. 11(a) and 11(b), there is a dependency of binding of aggregated BERIGLOBIN™ to Raji cells with an apparent optimum at pH 6.5 of the tested pH conditions. Lower pH conditions were not tested since a detrimental effect on cells is expected. It has thus to be made sure that only fresh medium with a pH at 7.0±0.25 is used for the tests. It is preferred to use FACS-buffer (HBSS+5% FCS+0.01% (w/v) Sodium azide, pH 6.5-6.8) in place of TM medium as diluent in the assay.

Example 6

The effect of monomeric human IgG on the competitive inhibition of IC binding to FcγRIIB positive cells by SM101 was tested in additional experiments. For this purpose Raji cells were either incubated with a set amount of aggregated BERIGLOBIN™ (2.5 μg/1×10⁵ cells) together with a set amount of monomeric BERIGLOBIN™ and varying amounts of SM101 (100, 50, 25, 12.5, 6.25, 3.12, 1.56, 0.78, 0.39 μM) or with a set amount of aggregated BERIGLOBIN™ and SM101 and varying amounts of monomeric BERIGLOBIN™ (3.3, 1.6, 0.8, 0.4, 0.2, 0.1, 0.05, 0 μM). Secondary antibody was added in excess (1/100 dilution of stock, 20 μL added to 1980 μL, protein concentration of sec. Ab: 0.5 μg/μL, equal to 0.25 μg/1×10⁵). It was found that monomeric BERIGLOBIN™ competitively inhibits binding of immune complexes to Raji cells in a nM concentration range. SM101 shows the same effect albeit in a μM concentration range. It can be concluded, that monomeric BERIGLOBIN™ binds to membrane-bound FcγRIIB thus inhibiting binding of aggregated BERIGLOBIN™. The number of aggregated and active BERIGLOBIN™ molecules in the system is not known, thus it is unclear whether the observed effect is due to a preferential binding of monomeric IgG to membrane-bound FcγRIIB or due to an outnumbering of aggregated BERIGLOBIN™ by added monomeric IgG. The highest concentration of monomeric IgG (3.3 μM) corresponds to 0.5 μg/1×10$^5$ cells, rendering it unlikely that monomeric IgG binds all available secondary antibody.

Example 7

In this experiment, the inter-/intraassay reproducibility concerning MFI of secondary antibody background was tested. In a retrospective analysis the data of n=25 tests were assessed for variations in the background staining of secondary antibody on Raji cells. In Table 6 (FIG. 15), the MFI of Raji cells stained with anti-human IgG(H+L)-PE secondary antibody (1/100 dilution), mean value of samples and standard deviation. Colours indicate experiments that were executed in parallel (intra-assay stability).

As can be seen from Table 6, the MFI of Raji cells stained with secondary antibody (without added aggregated BERIGLOBIN™) remains fairly constant when comparing either separate experiments (interassay stability) or parallel experiments (intraassay stability) with a standard deviation (SD) of 21% (SD MFI 29, Mean MFI 134.9).

Example 8

In this example, the inter-/intra-Assay reproducibility concerning apparent $K_D$ and $IC_{50}$ was tested. To assess the intra- and interassay stability of the FACS-based Potency Assay data sets from 25 experiments were analysed for the fitted apparent $K_D$ and $IC_{50}$. In FIG. 16 (Table 7), the $K_D$, $IC_{50}$ and cell density of Raji cells prior to harvest of 25 FACS-experiments is shown. Experiments 12-15 and 16-17 represent intrasassay stability since $K_D$ and $IC_{50}$ were assessed in separate tests on a single plate. Test #4 and 6 (highlighted in grey) have been excluded from subsequent analysis since the measured data were showing obvious outliers.

As can be concluded from the data shown in Table 7, interassay and intraassay stability is high. It has to be noted though, that starting with test #18 much lower $K_D$ and $IC_{50}$ values were determined. This correlates with a new Baseline-Setup of the FACS-Canto II machine.

Table 8 (FIG. 17) depicts the Mean value for the $K_D$ (0.53×10$^{-6}$M) and $IC_{50}$ (10.6 μg/mL) of all 25 experiments shown in Table 7. This leads to a SD of approx. 50% (SD=0.26). If calculating the Mean separately for tests #1-17 (excluding the obvious outliers #4 and 6) and #18-25 the SD is considerably lower at 29% for tests #1-17 (with a mean $K_D$ of 0.68×10$^{-6}$M), and at 26% for tests #18-25 (with a mean $K_D$ of 0.26×10$^{-6}$M) (Table 9; FIG. 18).

Table 9: Mean $K_D$ and $IC_{50}$ values of tests #1-17 and #18-25.

The invention claimed is:

1. An in vitro method for determining the stability of an investigational composition which comprises or consists essentially of at least one soluble human Fc gamma receptors selected from the group consisting of subtypes IIA, IIB, IIIA and IIIB, said method comprising the steps of:
   (a) obtaining an isolated human protein comprising aggregated human IgG from healthy human subjects wherein the human protein comprises at least 90% human IgG;
   (b) separating out monomeric and dimeric IgG from the human protein to obtain a non-heat aggregated human IgG;
   (c) contacting a surface comprising at least one soluble human Fc gamma receptor selected from the group consisting of subtypes IIA, IIB, IIIA and/or IIIB with a set amount of non-heat aggregated human IgG of step (b);
   (d) contacting said surface comprising at least one human Fc gamma receptor IIA, IIB, IIIA and/or IIIB of step (c) with a set amount of said investigational composition which comprises or consists essentially of at least one soluble human Fc gamma receptor selected from the group consisting of subtypes IIA, IIB, IIIA and IIIB, wherein the subtype of the human Fc gamma receptor comprised by said surface and the subtype of the human Fc gamma receptor comprised by said composition of soluble human Fc gamma receptor, is identical;
   (e) determining the amount of aggregated human IgG which is bound to said surface comprising said at least one of human Fc gamma receptors IIA, IIB, IIIA and IIIB; and
   (f) determining the stability of said investigational composition which comprises or consists essentially of at least one soluble human Fc gamma receptor selected from the group consisting of subtypes IIA, IIB, IIIA and IIIB by comparing the amount of aggregated human IgG of (e) with a reference value, wherein the reference value is the amount of non-heat aggregated human IgG which is bound to said surface comprising at least one soluble human Fc gamma receptor selected from the group consisting of subtypes IIA, IIB, IIIA, and IIIB previously determined by performing steps (a) through (e) using a reference composition comprising or consisting essentially of at least one soluble human Fc gamma receptor selected from the group consisting of subtypes IIA, IIB, IIIA, and IIIB; wherein the reference composition comprises identical soluble human Fc gamma receptor subtypes IIA, IIB, IIIA and/or IIIB as said investigational composition in the same amount; and wherein a decrease of the amount of non-heat aggregated human IgG bound to said surface of step (e) as compared to the reference value is indicative of the investigational composition being stable.

2. The method of claim 1, wherein said surface is selected from the group consisting of a mammalian cell and a solid surface that is coated with at least one of human Fc gamma receptors selected from the group consisting of subtypes IIA, IIB, IIIA and IIIB.

3. The method of claim 1, wherein said human protein of (a) comprises 95% or more human IgG.

4. The method of claim 1, wherein said non-heat aggregated human IgG of (b) is an aggregated human IgG that is obtained from human protein by an isolation method comprising size exclusion chromatography.

5. The method of claim 1, wherein said aggregated human IgG is labeled.

6. The method of claim 5, wherein said label comprises a secondary labeled human anti-IgG antibody.

7. The method of claim 1, wherein said at least one soluble human Fc gamma receptor is a soluble Fc gamma IIB receptor.

8. The method of claim 7, wherein said soluble human Fc gamma IIB receptor is SM101 consisting of SEQ ID No. 5

9. The method of claim 2, wherein said cell is a Raji cell as deposited under ATCC No. CCL-86.

\* \* \* \* \*

UNITED STATES PATENT AND TRADEMARK OFFICE
CERTIFICATE OF CORRECTION

| | | |
|---|---|---|
| PATENT NO. | : 10,866,247 B2 | Page 1 of 1 |
| APPLICATION NO. | : 14/909009 | |
| DATED | : December 15, 2020 | |
| INVENTOR(S) | : Peter Sondermann et al. | |

It is certified that error appears in the above-identified patent and that said Letters Patent is hereby corrected as shown below:

In the Claims

In Column 39, Line 5, in Claim 8, after "SEQ ID No." insert -- 1. --.

Signed and Sealed this
Fourteenth Day of February, 2023

*Katherine Kelly Vidal*

Katherine Kelly Vidal
*Director of the United States Patent and Trademark Office*

SEQUENCE LISTING

```
<160> NUMBER OF SEQ ID NOS: 10

<210> SEQ ID NO 1
<211> LENGTH: 177
<212> TYPE: PRT
<213> ORGANISM: artificial
<220> FEATURE:
<223> OTHER INFORMATION: soluble Fc gamma receptor IIB

<400> SEQUENCE: 1

Met Ala Pro Pro Lys Ala Val Leu Lys Leu Glu Pro Gln Trp Ile Asn
1               5                   10                  15

Val Leu Gln Glu Asp Ser Val Thr Leu Thr Cys Arg Gly Thr His Ser
            20                  25                  30

Pro Glu Ser Asp Ser Ile Gln Trp Phe His Asn Gly Asn Leu Ile Pro
        35                  40                  45

Thr His Thr Gln Pro Ser Tyr Arg Phe Lys Ala Asn Asn Asn Asp Ser
    50                  55                  60

Gly Glu Tyr Thr Cys Gln Thr Gly Gln Thr Ser Leu Ser Asp Pro Val
65                  70                  75                  80

His Leu Thr Val Leu Ser Glu Trp Leu Val Leu Gln Thr Pro His Leu
                85                  90                  95

Glu Phe Gln Glu Gly Glu Thr Ile Val Leu Arg Cys His Ser Trp Lys
            100                 105                 110

Asp Lys Pro Leu Val Lys Val Thr Phe Phe Gln Asn Gly Lys Ser Lys
        115                 120                 125

Lys Phe Ser Arg Ser Asp Pro Asn Phe Ser Ile Pro Gln Ala Asn His
    130                 135                 140

Ser His Ser Gly Asp Tyr His Cys Thr Gly Asn Ile Gly Tyr Thr Leu
145                 150                 155                 160
```

```
Tyr Ser Ser Lys Pro Val Thr Ile Thr Val Gln Ala Pro Ser Ser Ser
                165                 170                 175

Pro

<210> SEQ ID NO 2
<211> LENGTH: 534
<212> TYPE: DNA
<213> ORGANISM: artificial
<220> FEATURE:
<223> OTHER INFORMATION: soluble Fc gamma receptor IIB

<400> SEQUENCE: 2
atggcaccgc cgaaagcagt tctgaaactg gaaccgcagt ggattaacgt tctgcaggaa      60
gatagcgtta ccctgacctg tcgtggcacc catagcccgg aaagcgatag cattcagtgg     120
tttcacaacg gcaatctgat tccgacccat acccagccga gctatcgttt taaagcgaac     180
aacaacgata gcggcgaata tacctgtcag accggtcaga ccagcctgag cgatccggtt     240
catctgaccg ttctgagcga atggctggtt ctgcagaccc cgcatctgga atttcaggaa     300
ggcgaaacca ttgttctgcg ttgccacagc tggaaagata aaccgctggt taaagttacc     360
ttcttccaga acggcaaaag caaaaaattc agccgtagcg atccgaattt tagcattccg     420
caggcgaatc atagccatag cggcgattat cattgtaccg gcaacattgg ctatacc ctg     480 tatagcagca aaccggtgac cattaccgtt caggcgccga gcagcagccc gtaa          534

<210> SEQ ID NO 3
<211> LENGTH: 181
<212> TYPE: PRT
<213> ORGANISM: human
<220> FEATURE:
<221> NAME/KEY: misc_feature
<222> LOCATION: (1)..(181)
<223> OTHER INFORMATION: human Fc gamma RIIB

<400> SEQUENCE: 3

Met Gly Thr Pro Ala Ala Pro Pro Lys Ala Val Leu Lys Leu Glu Pro
1               5                   10                  15

Gln Trp Ile Asn Val Leu Gln Glu Asp Ser Val Thr Leu Thr Cys Arg
            20                  25                  30

Gly Thr His Ser Pro Glu Ser Asp Ser Ile Gln Trp Phe His Asn Gly
        35                  40                  45

Asn Leu Ile Pro Thr His Thr Gln Pro Ser Tyr Arg Phe Lys Ala Asn
    50                  55                  60

Asn Asn Asp Ser Gly Glu Tyr Thr Cys Gln Thr Gly Gln Thr Ser Leu
65                  70                  75                  80

Ser Asp Pro Val His Leu Thr Val Leu Ser Glu Trp Leu Val Leu Gln
                85                  90                  95

Thr Pro His Leu Glu Phe Gln Glu Gly Glu Thr Ile Val Leu Arg Cys
            100                 105                 110

His Ser Trp Lys Asp Lys Pro Leu Val Lys Val Thr Phe Phe Gln Asn
        115                 120                 125

Gly Lys Ser Lys Lys Phe Ser Arg Ser Asp Pro Asn Phe Ser Ile Pro
    130                 135                 140

Gln Ala Asn His Ser His Ser Gly Asp Tyr His Cys Thr Gly Asn Ile
145                 150                 155                 160

Gly Tyr Thr Leu Tyr Ser Ser Lys Pro Val Thr Ile Thr Val Gln Ala
                165                 170                 175

Pro Ser Ser Ser Pro
```

<210> SEQ ID NO 4
<211> LENGTH: 543
<212> TYPE: DNA
<213> ORGANISM: human
<220> FEATURE:
<221> NAME/KEY: misc_feature
<222> LOCATION: (1)..(5443)
<223> OTHER INFORMATION: human Fc gamma RIIB

<400> SEQUENCE: 4

```
atggggacac ctgcagctcc cccaaaggct gtgctgaaac tcgagcccca gtggatcaac      60
gtgctccagg aggactctgt gactctgaca tgccggggga ctcacagccc tgagagcgac     120
tccattcagt ggttccacaa tgggaatctc attcccaccc acacgcagcc cagctacagg     180
ttcaaggcca acaacaatga cagcggggag tacacgtgcc agactggcca gaccagcctc     240
agcgaccctg tgcatctgac tgtgctttct gagtggctgg tgctccagac ccctcacctg     300
gagttccagg agggagaaac catcgtgctg aggtgccaca ctggaaggga caagcctctg     360
gtcaaggtca cattcttcca gaatggaaaa tccaagaaat tttcccgttc ggatcccaac     420
ttctccatcc acaagcaaa ccacagtcac agtggtgatt accactgcac aggaaacata     480
ggctacacgc tgtactcatc caagcctgtg accatcactg tccaagctcc cagctcttca     540
ccg                                                                   543
```

<210> SEQ ID NO 5
<211> LENGTH: 184
<212> TYPE: PRT
<213> ORGANISM: human
<220> FEATURE:
<221> NAME/KEY: misc_feature
<222> LOCATION: (1)..(184)
<223> OTHER INFORMATION: human Fc gamma RIIA

<400> SEQUENCE: 5

```
Met Gly Thr Pro Ala Ala Pro Pro Lys Ala Val Leu Lys Leu Glu Pro
1               5                   10                  15

Pro Trp Ile Asn Val Leu Gln Glu Asp Ser Val Thr Leu Thr Cys Gln
            20                  25                  30

Gly Ala Arg Ser Pro Glu Ser Asp Ser Ile Gln Trp Phe His Asn Gly
        35                  40                  45

Asn Leu Ile Pro Thr His Thr Gln Pro Ser Tyr Arg Phe Lys Ala Asn
    50                  55                  60

Asn Asn Asp Ser Gly Glu Tyr Thr Cys Gln Thr Gly Gln Thr Ser Leu
65                  70                  75                  80

Ser Asp Pro Val His Leu Thr Val Leu Ser Glu Trp Leu Val Leu Gln
                85                  90                  95

Thr Pro His Leu Glu Phe Gln Glu Gly Glu Thr Ile Met Leu Arg Cys
            100                 105                 110

His Ser Trp Lys Asp Lys Pro Leu Val Lys Val Thr Phe Phe Gln Asn
        115                 120                 125

Gly Lys Ser Gln Lys Phe Ser His Leu Asp Pro Thr Phe Ser Ile Pro
    130                 135                 140

Gln Ala Asn His Ser His Ser Gly Asp Tyr His Cys Thr Gly Asn Ile
145                 150                 155                 160

Gly Tyr Thr Leu Phe Ser Ser Lys Pro Val Thr Ile Thr Val Gln Val
                165                 170                 175
```

Pro Ser Met Gly Ser Ser Ser Pro
            180

<210> SEQ ID NO 6
<211> LENGTH: 554
<212> TYPE: DNA
<213> ORGANISM: human
<220> FEATURE:
<221> NAME/KEY: misc_feature
<222> LOCATION: (1)..(554)
<223> OTHER INFORMATION: human Fc gamma RIIA

<400> SEQUENCE: 6

```
atggggacac ctgcagctcc cccaaaggct gtgctgaaac ttgagccccc gtggatcaac      60
gtgctccagg aggactctgt gactctgaca tgccaggggg ctcgcagccc tgagagcgac     120
tccattcagt ggttccacaa tgggaatctc attcccaccc acacgcagcc cagctacagg     180
ttcaaggcca acaacaatga cagcggggag tacacgtgcc agactggcca gaccagcctc     240
agcgaccctg tgcatctgac tgtgctttcc aatggctggt gctccagac ccctcacctg      300
gagttccagg agggagaaac catcatgctg aggtgccaca gctggaagga caagcctctg     360
gtcaaggtca cattcttcca gaatggaaaa tcccagaaat ctccccattt ggatcccacc     420
ttctccatcc acaagcaaa ccacagtcac agtggtgatt accactgcac aggaaacata      480
ggctacacgc tgttctcatc caagcctgtg accatcactg tccaagtgcc agcatgggc      540
agctcttcac caat                                                      554
```

<210> SEQ ID NO 7
<211> LENGTH: 182
<212> TYPE: PRT
<213> ORGANISM: human
<220> FEATURE:
<221> NAME/KEY: misc_feature
<222> LOCATION: (1)..(182)
<223> OTHER INFORMATION: human Fc gamma RIIIA

<400> SEQUENCE: 7

Met Asp Leu Pro Lys Ala Val Val Phe Leu Glu Pro Gln Trp Tyr Arg
1               5                   10                  15

Val Leu Glu Lys Asp Ser Val Thr Leu Lys Cys Gln Gly Ala Tyr Ser
            20                  25                  30

Pro Glu Asp Asn Ser Thr Gln Trp Phe His Asn Glu Ser Leu Ile Ser
        35                  40                  45

Ser Gln Ala Ser Ser Tyr Phe Ile Asp Ala Ala Thr Val Asp Asp Ser
    50                  55                  60

Gly Glu Tyr Arg Cys Gln Thr Asn Leu Ser Thr Leu Ser Asp Pro Val
65                  70                  75                  80

Gln Leu Glu Val His Ile Gly Trp Leu Leu Leu Gln Ala Pro Arg Trp
                85                  90                  95

Val Phe Lys Glu Glu Asp Pro Ile His Leu Arg Cys His Ser Trp Lys
            100                 105                 110

Asn Thr Ala Leu His Lys Val Thr Tyr Leu Gln Asn Gly Lys Gly Arg
        115                 120                 125

Lys Tyr Phe His His Asn Ser Asp Phe Tyr Ile Pro Lys Ala Thr Leu
    130                 135                 140

Lys Asp Ser Gly Ser Tyr Phe Cys Arg Gly Leu Val Gly Ser Lys Asn
145                 150                 155                 160

Val Ser Ser Glu Thr Val Asn Ile Thr Ile Thr Gln Gly Leu Ser Val
                165                 170                 175

Ser Thr Ile Ser Ser Phe
            180

<210> SEQ ID NO 8
<211> LENGTH: 546
<212> TYPE: DNA
<213> ORGANISM: human
<220> FEATURE:
<221> NAME/KEY: human
<222> LOCATION: (1)..(546)
<223> OTHER INFORMATION: human Fc gamma RIIIA

<400> SEQUENCE: 8

```
atggatctcc caaaggctgt ggtgttcctg gagcctcaat ggtacagggt gctcgagaag     60
gacagtgtga ctctgaagtg ccagggagcc tactccctg aggacaattc cacacagtgg    120
tttcacaatg agagcctcat ctcaagccag gcctcgagct acttcattga cgctgccaca   180
gttgacgaca gtggagagta caggtgccag acaaacctct ccaccctcag tgacccggtg   240
cagctagaag tccatatcgg ctggctgttg ctccaggccc ctcggtgggt gttcaaggag   300
gaagacccta ttcacctgag gtgtcacagc tggaagaaca ctgctctgca taaggtcaca   360
tatttacaga tggcaaagg caggaagtat tttcatcata attctgactt ctacattcca   420
aaagccacac tcaaagacag cggctcctac ttctgcaggg ggcttgttgg gagtaaaaat   480
gtgtcttcag agactgtgaa catcaccatc actcaaggtt tgtcagtgtc aaccatctca   540
tcattc                                                              546
```

<210> SEQ ID NO 9
<211> LENGTH: 182
<212> TYPE: PRT
<213> ORGANISM: human
<220> FEATURE:
<221> NAME/KEY: misc_feature
<222> LOCATION: (1)..(182)
<223> OTHER INFORMATION: human Fc gamma RIIIB

<400> SEQUENCE: 9

Met Asp Leu Pro Lys Ala Val Val Phe Leu Glu Pro Gln Trp Tyr Ser
1               5                   10                  15

Val Leu Glu Lys Asp Ser Val Thr Leu Lys Cys Gln Gly Ala Tyr Ser
            20                  25                  30

Pro Glu Asp Asn Ser Thr Gln Trp Phe His Asn Glu Asn Leu Ile Ser
        35                  40                  45

Ser Gln Ala Ser Ser Tyr Phe Ile Asp Ala Ala Thr Val Asn Asp Ser
    50                  55                  60

Gly Glu Tyr Arg Cys Gln Thr Asn Leu Ser Thr Leu Ser Asp Pro Val
65                  70                  75                  80

Gln Leu Glu Val His Ile Gly Trp Leu Leu Leu Gln Ala Pro Arg Trp
                85                  90                  95

Val Phe Lys Glu Glu Asp Pro Ile His Leu Arg Cys His Ser Trp Lys
            100                 105                 110

Asn Thr Ala Leu His Lys Val Thr Tyr Leu Gln Asn Gly Lys Asp Arg
        115                 120                 125

Lys Tyr Phe His His Asn Ser Asp Phe His Ile Pro Lys Ala Thr Leu
    130                 135                 140

Lys Asp Ser Gly Ser Tyr Phe Cys Arg Gly Leu Val Gly Ser Lys Asn
145                 150                 155                 160

Val Ser Ser Glu Thr Val Asn Ile Thr Ile Thr Gln Gly Leu Ala Val

```
                    165                 170                 175
Ser Thr Ile Ser Ser Phe
            180

<210> SEQ ID NO 10
<211> LENGTH: 486
<212> TYPE: DNA
<213> ORGANISM: human
<220> FEATURE:
<221> NAME/KEY: misc_feature
<222> LOCATION: (1)..(486)
<223> OTHER INFORMATION: human Fc gamma RIIIB

<400> SEQUENCE: 10
gacagtgtga ctctgaagtg ccagggagcc tactccctg aggacaattc cacacagtgg      60
tttcacaatg agaacctcat ctcaagccag gcctcgagct acttcattga cgctgccaca    120
gtcaacgaca gtggagagta caggtgccag acaaacctct ccaccctcag tgacccggtg    180
cagctagaag tccatatcgg ctggctgttg ctccaggccc ctcggtgggt gttcaaggag    240 gaagaccta ttcacctgag gtgtcacagc tggaagaaca ctgctctgca taaggtcaca     300
tatttacaga atggcaaaga caggaagtat tttcatcata attctgactt ccacattcca    360
aaagccacac tcaaagatag cggctcctac ttctgcaggg ggcttgttgg gagtaaaaat    420
gtgtcttcag agactgtgaa catcaccatc actcaaggtt tggcagtgtc aaccatctca    480
tcattc                                                               486
```